United States Patent [19]

Guthrie et al.

[11] 4,354,039
[45] Oct. 12, 1982

[54] CHLOROCITRIC ACIDS

[75] Inventors: Robert W. Guthrie, Saddle Brook; Richard W. Kierstead, North Caldwell; Francis A. Mennona, Nutley; Ann C. Sullivan, Cedar Grove, all of N.J.

[73] Assignee: Hoffmann-La Roche Inc., Nutley, N.J.

[21] Appl. No.: 304,407

[22] Filed: Sep. 21, 1981

Related U.S. Application Data

[62] Division of Ser. No. 973,504, Dec. 26, 1978.

[51] Int. Cl.$^3$ .................. C07C 59/245; C07C 59/265
[52] U.S. Cl. ..................................... 562/582; 562/584
[58] Field of Search ............................. 562/582, 584

[56]         References Cited
          U.S. PATENT DOCUMENTS 3,769,338 10/1973 Dagoni et al. .................. 562/584
3,769,338 10/1973 Dagoni et al. .................. 562/582
3,770,796 11/1973 Lawrence, Jr. et al. .......... 562/584
3,843,711 10/1974 Wiegand ............................. 562/584
3,965,168  6/1976 Wiegand ............................. 562/584

Primary Examiner—Paul J. Killos
Attorney, Agent, or Firm—Jon S. Saxe; Bernard S. Leon; James H. Callwood

[57]            ABSTRACT

The present invention relates to chlorocitric acids of the formula

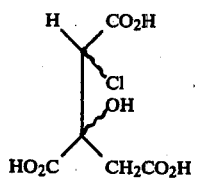

and stereoisomers, optical antipodes and pharmaceutically acceptable salts thereof, to methods of preparation thereof, including intermediates involved therein, and to their use as anorectic agents for the treatment of obesity in mammals.

10 Claims, No Drawings

CHLOROCITRIC ACIDS

This is a division of application Ser. No. 973,504, filed Dec. 26, 1978.

BACKGROUND OF THE INVENTION

In the continuing war against obesity several derivatives of citric acid, which have been implicated in fatty acid synthesis (see, for example, A. C. Sullivan et al., Lipids, 9, 121 [1974]), have been prepared with the hope of developing a medicinal agent effective against the disease and devoid of undesirable side effects.

Hydroxycitric acids reduce food intake and body weight gain by suppressing appetite and inhibiting fatty acid synthesis (A. C. Sullivan et al., Am. J. Clin. Nutr., 30, 767 [1977]). Aminocitric acids are useful in the treatment of obesity by inhibiting lipogenesis (R. W. Guthrie and R. W. Kierstead, U.S. Pat. No. 3,960,933 [issued June 1, 1976]), as are the ester and amide derivatives of hydroxycitric acid α-lactone (R. W. Guthrie and R. W. Kierstead, U.S. Pat. No. 3,993,668 [issued Nov. 23, 1976]).

Of the halocitric acids, the fluoro compounds, potent inhibitors of aconitate hydratase, have been found to be too toxic to be useful in the control of obesity (R. J. Dummell and E. Kun, J. Biol. Chem., 244, 2966 (1969)). Chlorocitric acids have been reported in the scientific and patent literature. D. Pawolleck in Ann., 178, 150 (1875) stated his intention to prepare "monochlorocitric acid" at page 152 and claimed the formation of a "chlorine containing acid" by the addition of hypochlorous acid to aconitic acid at page 156. By application of Pawolleck's method, C. Martius and R. Mave, Z. Physiol. Chem., 269, 23 (1941) claimed that only chlorine-free products were obtained. Recently, C. L. Mehltretter, in U.S. Pat. No. 3,536,630 (issued Oct. 27, 1970) reported that substitution of chlorine for hypochlorous acid in Pawolleck's procedure affords a solution of "disodiumchlorohydroxytricarballylate" in water. Biological properties of the alleged chlorocitric acids were not disclosed. It has now been found that repetition of the prior methods for the addition of hypochlorous acid or chlorine to aconitic acid give only non-chlorine containing products.

Iodo- and bromocitric acids have not been described.

DESCRIPTION OF THE INVENTION

The present invention relates to chlorocitric acids of the formula

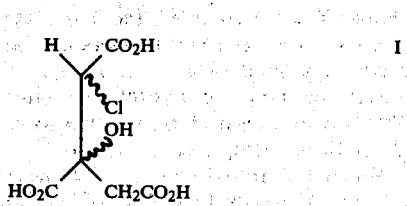

and steroisomers, optical antipodes and pharmaceutically acceptable salts thereof, to methods of preparation thereof, including intermediates involved therein, and to their use as anorectic agents in the treatment of obesity.

More specifically, the present invention relates to (±)-erythro-chlorocitric acid, (±)-threo-chlorocitric acid, (+)-erythro-chlorocitric acid, (−)-erythro-chlorocitric acid, (+)-threo-chlorocitric acid, to methods of preparation thereof involving the addition of the elements of hypochlorous acid to trans-aconitic acid to afford (±)-threo-chlorocitric acid, β-lactone, which is hydrolyzed to (±)-threo-chlorocitric acid, the addition of the elements of hypochlorous acid to cis-aconitic acid to afford (±)-erythro-chlorocitric acid and (±)-threo-chlorocitric acid, β-lactones which are hydrolyzed to (±)-threo-chlorocitric acid, the acid-induced cleavage of (±)-threo- and (±)-erythro-epoxyaconitic acid by alkali metal chloride to (±)-threo-chlorocitric acid and (±)-erythro-chlorocitric acid, respectively, or alternatively, and more efficiently, the epoxidation of cis-aconitic acid, or the anhydride thereof, in alkaline medium to a partial salt of (±)-erythro-epoxyaconitic acid, which is cleaved by alkali metal chloride in the presence of acid to (±)-erythro-chlorocitric acid, the acid-induced cleavage of (+)-threo-epoxyaconitic acid by alkali metal chloride to (−)-threo-chlorocitric acid, the acid-induced cleavage of (−)-threo-epoxyaconitic acid by alkali metal chloride to (+)-threo-chlorocitric acid, the acid-induced cleavage of (−)-erythro-epoxyaconitic acid by alkali metal chloride to (+)-erythro-chlorocitric acid, and the acid-induced cleavage of (+)-erythro-epoxyaconitic acid by alkali metal chloride to (−)-erythro-chlorocitric acid, and to their usefulness as anorectic agents delaying gastric emptying without concomitant metabolic effects on cholesterol or lipid synthesis in the treatment of obesity.

Additionally, the present invention relates to the isolable and characterizable mono-salts of (±)-threo-epoxyaconitic acid and its utility in the synthesis of (±)-threo- and (−)-threo-chlorocitric acid involving, respectively, the acid-induced cleavage of the mono-salts of (±)-threo-epoxyaconitic acid to (±)-threo-chlorocitric acid and the neutralization of the mono-salts of (±)-threo-epoxyaconitic acid to (±)-threo-epoxyaconitic acid followed by optical resolution to (+)-threo-epoxyaconitic acid and acid-induced cleavage to (−)-threo-chlorocitric acid.

The present invention also relates to a process for the resolution of (±)-erythro-chlorocitric acid employing sequentially (−)-p-nitro-α-methylbenzylamine and (+)-p-nitro-α-methylbenzylamine and to the diastereoisometric salts, (+)-erythro-chlorocitric acid bis R-(−)-αmethyl-p-nitrobenzylamine and (−)-erythro-chlorocitric acid bis R-(+)-α-methyl-p-nitrobenzylamine formed thereby.

As used throughout the specification and appended claims, the terms "alkali metal" and "alkaline earth metal" refer to lithium, sodium and potassium, and calcium, respectively. The term "alkanol" refers to the compound derived by replacement of a proton of a straight or branched chain alkane having 1 to 20 carbon atoms by a hydroxyl moiety. Examples of alkanols include methanol, ethanol, 2-propanol and the like. The term "alkanoic acid" refers to the compound derived by replacement of the two protons bound to the carbon atom bearing the hydroxyl moiety of an alkanol by a carbonyl function. The term "lower" as applied to the aforementioned groups refers to those groups having 1 to 8 carbon atoms.

The compounds of the present invention, namely, the chlorocitric acids of formula I and the chlorocitric acid, β-lactones of formula IV, as well as certain starting materials and intermediates in the preparation thereof, bear two asymmetric centers and thus exist in two relative stereochemical forms: a threo form and an erythro form. Each form, i.e., the threo form and erythro form, can exist as a racemate and two optical antipodes, one rotating a beam of polarized light clockwise and the other counterclockwise, the former being designated the (+)-optical antipode, the latter the (−)-optical isomer and the racemate the (±)-system. In conjunction therewith, the threo-erythro nomenclature as defined by D. C. Cram and F. A. A. Elhafez. J. Amer. Chem. Soc., 74, 5828 (1952) and R. S. Cahn, et al., Experientia, 12, 81 (1956) has been adopted to facilitate the description of the compound, process and methods described herein. Thus, for example, the chlorocitric acids of the present invention are described as the (±)-erythro-, (+)-erythro-, (−)-erythro, (±)-threo, (+)-threo- and (−)-threo-isomers.

While the compounds, processes and methods of the present invention are generally depicted for each stereoisomer, a wiggly line attaching chloro atom or hydroxyl group to the citric acid skeleton has been employed to denote all possible orientations of these functions about the asymmetric centers.

(±)-threo-Chlorocitric acid of the formula

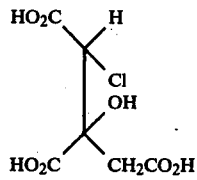

can be prepared by adding the elements of hypochlorous acid across the carbon-to-carbon double bond of commercially available trans-aconitic acid of the formula

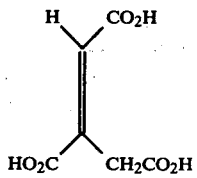

to form (±)-threo-chlorocitric acid, β-lactone of the formula

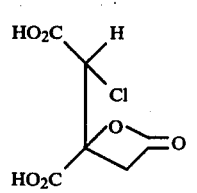

the β-lactone function of which is hydrolyzed to afford the hydroxyacid II.

The chlorohydrination is conveniently performed by dissolving the aconitic acid III in an aqueous solution of an alkali metal hydroxide such as lithium, sodium or potassium hydroxide, preferably sodium or potassium hydroxide, containing a sufficient amount of alkali metal to form a salt of trans-aconitic acid of the formula

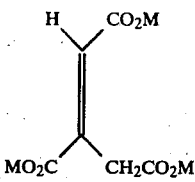

wherein M is an alkali metal, cooling the solution to about 0° C. to about 20° C., preferably to about 5° C., treating the solution with excess chlorine or hypochlorous acid, preferably chlorine, to form a (±)-threo-chlorocitric acid, -lactone salt of the formula

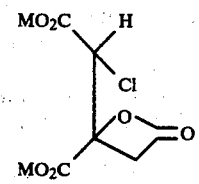

wherein M is an alkali metal and acidifying the salt VI to the acid IV.

Suitable aqueous solvents for the chlorohydrination include water and mixtures of water and lower alkanols such as methanol, ethanol, 2-propanol and the like, water and ethers such as dimethoxyethane, tetrahydrofuran and dioxane, and water and polar aprotic solvents such as dimethylacetamide, dimethylformamide, dimethylsulfoxide and hexamethylphosphoramide.

Among acids suitable for the conversion of the dialkali metal salt of (±)-threo-chlorocitric acid, β-lactone of formula VI to the corresponding free acid of formula IV may be mentioned mineral acids, for example, hydrochloric acid, sulfuric acid, nitric acid, phosphoric acid and the like, sulfonic acids such as methanesulfonic acid, phenylsulfonic acid, p-toluenesulfonic acid and the like and strong organic acids such as trifluoroacetic acid, trichloroacetic acid and the like.

The hydrolysis of the β-lactone function of the diacid of formula IV or the dialkali metal salt thereof of formula VI is accomplished by suspending or dissolving the diacid or the disalt in an aqueous solvent containing an acid such as those employed for the acidification of the disalt VI to the diacid IV and heating the resulting reaction system to a temperature of about 30° C. to about 80° C. to complete the hydrolysis, which, while relatively slow at room temperature, nevertheless proceeds at a synthetically useful rate at a temperature within this range. A hydrolysis temperature of about 50° C. to 70° C. is preferred, a hydrolysis temperature of about 70° C. being most preferred.

While chlorohydrination of trans-aconitic acid of formula III and the hydrolysis of (±)-threo-chlorocitric acid, β-lactone of formula IV may be performed stepwise, it is more convenient and efficient to acidify the dialkali metal salt of formula VI and heat the resulting reaction mixture to complete the hydrolysis of the diacid IV to afford (±)-threo-chlorocitric acid. Thus, upon completion of the chlorohydrination of the aconitic acid of formula III, the reaction mixture is acidified with an acid, preferably a mineral acid, most preferably hydrochloric acid, and heated from about 30° C. to about 100° C., preferably from about 50° C. to about 90° C., most preferably at about 70° C., to complete the conversion of the β-lactone function of formula IV to the hydroxyacid moiety of formula II.

On the basis of the foregoing, one would have anticipated the formation of (±)-erythro-chlorocitric acid of the formula

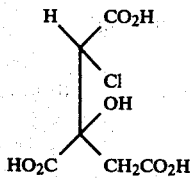

VII via (±)-erythro-chlorocitric acid, β-lactone of the formula

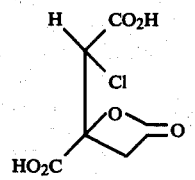

VIII by application of the hereinbefore described hypochlorination sequence to cis-aconitic acid of the formula

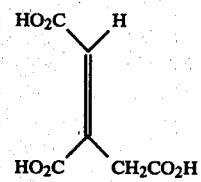

IX

Unexpectedly, the product after acidification of the reaction is mainly a mixture of (±)-Threo-chlorocitric acid, β-lactone apparently formed by epimerization of the highly strained (±)-erythro-chlorocitric acid, β-lactone, and (±)-threo-chlorocitric acid, (±)-Erythro-chlorocitric acid was formed only in trace amounts.

Alternatively, and more efficiently, (±)-erythro-chlorocitric acid (VII) is prepared in a high yield process involving the cleavage of the epoxide ring of (±)-eythro-epoxyaconitic acid of the formula

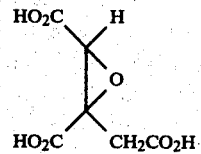

X generated in situ by the epoxidation of cis-aconitic acid (IX) or the corresponding anhydride of the formula

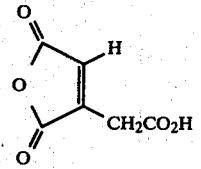

XI

The epoxidation is readily performed utilizing hydrogen peroxide in conjunction with an epoxidation catalyst. A particularly effective epoxidation catalyst is tungstic acid or a salt thereof, preferably an alkali metal salt, most preferably the sodium salt. While the epoxidation is preferably carried out in water, containing about 0 molar equivalents to about 2.9 molar equivalents of an alkali metal hydroxide, such as lithium, sodium or potassium hydroxide, preferably about 2.5 molar equivalents of sodium hydroxide, an organic solvent such as lower alkanol, for example, methanol, ethanol or 2-propanol, or a water soluble ether such as dimethoxyethane, tetrahydrofuran or dioxane, may be employed as a diluent. The epoxidation is conveniently performed at a reaction temperature of about 0° C. to about 100° C. To minimize conversion of cis-aconitic acid X or its anhydride XI to the trans-isomer III, however, it is preferable to perform the epoxidation at a temperature within the range of about 20° C. to about 50° C.

Without isolation, the resulting (±)-erythro-epoxyaconitic acid X or the salt thereof of the formula

XII wherein M is an alkali metal and R is hydrogen or M is acidified and then cleaved by treatment with an alkali metal chloride such as lithium, sodium or potassium chloride, preferably sodium chloride. Suitable acids include mineral acids, for example, hydrochloric acid, sulfuric acid, phosphoric acid and the like, sulfonic acids such as methanesulfonic acid, phenylsulfonic acid, p-toluenesulfonic acid and the like, and strong organic acids such as trifluoroacetic acid, trichloroacetic and the like. Hydrochloric acid is preferred.

To avoid possible side reactions involving carboxylate ions of the so-formed chloroacid VII, it is desirable to perform the cleavage in the presence of about one molar equivalent to about 10 molar equivalents of the abovementioned acids. Thus, when the epoxidation is carried out in the absence of an alkali metal hydroxide, it is desirable to employ about one molar equivalent to about 10 molar equivalents of acid, and when the epoxidation is accomplished in the presence of about 2.5 molar equivalents of alkali metal hydroxide, it is desirable to utilize about 3.5 molar equivalents to about 12.5 molar equivalents of acid. One molar equivalent to 3.5 molar equivalents of acid is preferred.

The epoxide cleavage is usually conducted at a temperature resulting in a convenient reaction rate. While not narrowly critical, the cleavage reaction temperature is normally maintained within the range of about 50° C. to about 80° C., preferably at about 70° C., to avoid undesired side reactions of the chloroacid so-formed.

While the aforedescribed process for the preparation of (±)-erythro-chlorocitric acid (VII) is efficiently performed by cleaving the (±)-erythro-epoxyaconitic acid X generated in situ, the erythro-epoxy acid X, prepared and isolated by the method disclosed by R. W. Guthrie et al., U.S. Pat. No. 3,969,772, issued June 29, 1976, may also be cleaved to the erythro-chloroacid VII as hereinbefore described for the in situ process, i.e., by an alkali metal chloride dissolved in an aqueous solvent in the presence of an acid, preferably by excess sodium chloride in the presence of about one mole of hydrochloric acid in water, most preferably at a temperature of about 70° C.

Similarly, (±)-threo-epoxyaconitic acid of the formula

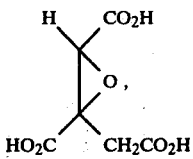    XIII which may be prepared as described in R. W. Guthrie et al., U.S. Pat. No. 3,966,772, issued June 29, 1976, is cleaved by an alkali metal chloride dissolved in an aqueous solvent in the presence of an acid, preferably by excess sodium chloride dissolved in water in the presence of one molar equivalent of hydrochloric acid at a temperature within the range of about 50° C. to about 80° C., most preferably at a temperature of about 70° C., to afford (±)-threo-chlorocitric acid (II).

Likewise, (+)-threo-epoxyaconitic acid of the formula

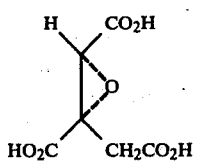    XIV is cleaved to (−)-threo-chlorocitric acid of the formula

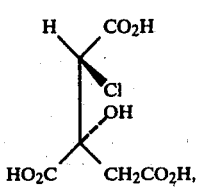    XV (−)-threo-epoxyaconitic acid of the formula

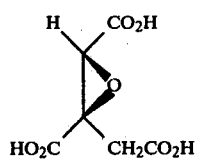    XVI is cleaved to (+)-threo-chlorocitric acid of the formula

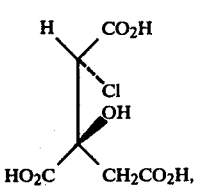    XVII (−)-erythro-epoxyaconitic acid of the formula

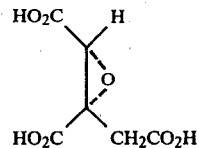    XVIII is cleaved to (+)-erythro-chlorocitric acid of the formula

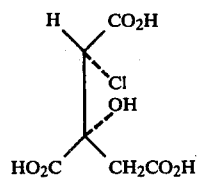    XIX and (+)-erythro-epoxyaconitic acid of the formula

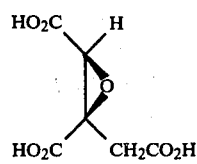    XX is cleaved to (−)-erythro-chlorocitric acid of the formula

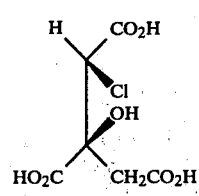    XXI by an alkali metal chloride dissolved in an aqueous solvent in the presence of an acid, preferably by excess sodium chloride dissolved in water in the presence of one molar equivalent of hydrochloric acid at a temperature within the range of about 50° C. to about 80° C., most preferably at a temperature of about 70° C.

The synthesis of (+)-threo- and (−)-threo-epoxyaconitic acid by optical resolution procedures is described in R. W. Guthrie et al. U.S. Pat. No. 3,966,772 issued June 29, 1976.

(−)-erythro-Epoxyaconitic acid (XVIII) is prepared from crystalline (−)-threo-hydroxycitric acid of the formula

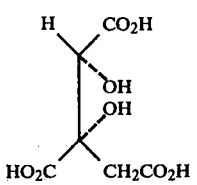    XXII via trimethyl(−)-threo-mesyloxycitrate of the formula

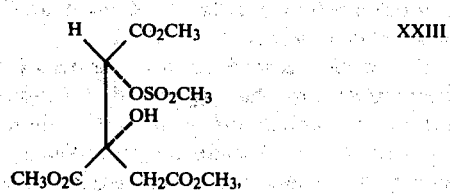

the preparation of which is disclosed in R. W. Guthrie et al. U.S. Pat. No. 3,966,772 issued June 29, 1976, by a process involving partial hydrolysis of the carboxylic acid ester groups of the citrate XXIII to a mixture (ca 1:1) of (−)-threo-mesyloxycitric acid of the formula

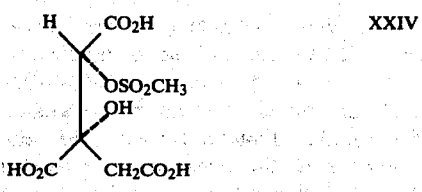

and methyl(−)-threo-mesyloxycitrate of the formula

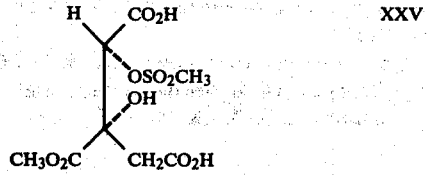

followed by displacement of the mesyloxy group of the di- and tricarboxylic acid XXIV and XXV to form the epoxy function of XVIII and saponification of the remaining carboxylic ester group of XXV to complete the synthesis.

The partial hydrolysis is accomplished by treating the mesyloxy tricarboxylic acid ester XXIII with a mineral acid such as hydrobromic acid, hydrochloric acid, sulfuric acid, nitric acid and the like in a water miscible solvent. Suitable water miscible solvents include lower alkanols such as methanol, ethanol, 2-propanol and the like, and lower alkanoic acids such as formic, acetic and propionic acids. The acid-solvent combination of hydrochloric acid-acetic acid is preferred.

To avoid formation of (−)-erythro-hydroxycitric acid,α-lactone of the formula

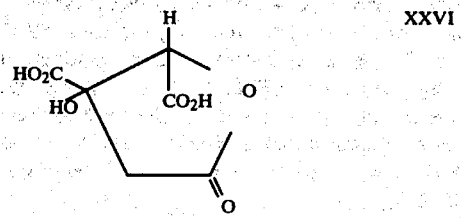

the hydrolysis is preferably performed at a reaction temperature of about 80° C. for about 24 hours.

The internal displacement of the mesyloxy group of the tricarboxylic acid XXIV and dicarboxylic acid monocarboxylic acid ester XXV with inversion to form the oxirane ring of XVIII and the saponification of the carboxylic acid ester group of XXV is conveniently carried out according to the method described by R. W. Guthrie et al. in U.S. Pat. No. 3,966,772 issued June 29, 1976.

Application of the esterification, mesylation, partial hydrolysis and internal displacement-saponification sequence to (+)-threo-hydroxycitric acid of the formula

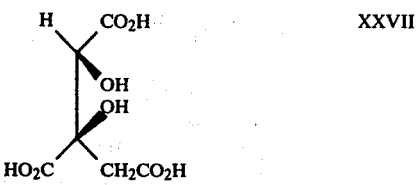

affords (+)-erythro-epoxyaconitic acid (XX).

Crystalline (−)-threo-hydroxycitric acid (XXII) is readily prepared from aminoethyleneammonium(−)-threo-hydroxycitrate of the formula

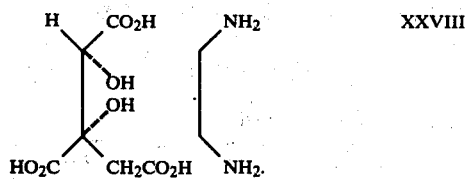

the synthesis of which is reported in U.S. patent application Ser. No. 667,317 filed Mar. 16, 1976, now abandoned, by acidifying the salt XXVIII with aqueous trifluoroacetic acid, from which the hydroxy acid XXII crystallizes at a temperature within the range of about 5° C. to about 10° C. and isolating the product by filtration.

While the optically active chlorocitric acids of the present invention are more readily prepared by chlorinolysis of the oxirane ring of optically active epoxyaconitic acid, as hereinbefore described, these compounds may also be prepared from racemic threo- and erythro-chlorocitric acids by resolution methods known in the art. For example, by employing (+)-p-nitro-α-methylbenzylamine and (−)-p-nitro-αmethylbenzylamine sequentially as the resolving agents, (±)-erythro-chlorocitric acid (VII) may be resolved into its optical antipodes, (+)-erythro-chlorocitric acid (XIX) and (−)-erythro-chlorocitric acid (XXI), by separation of the diastereoisomeric salts of the formulas

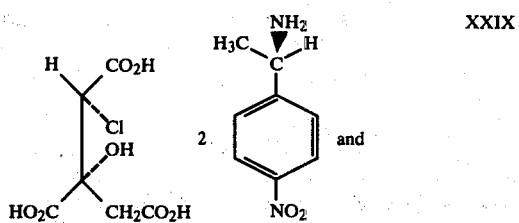

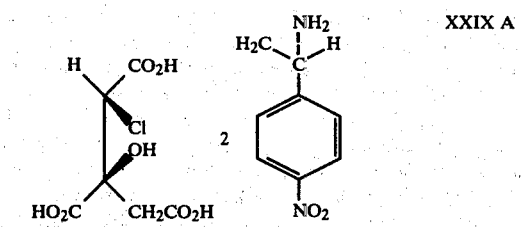

so formed according to the procedure outlined in U.S. Pat. No. 3,901,915 issued Aug. 26, 1975.

In an additional and highly efficient synthesis of (±)-threo-chlorocitric acid (II), trans-aconitic acid (III) is converted to its readily isolable and characterizable, highly crystalline-mono-alkali metal salt XXX

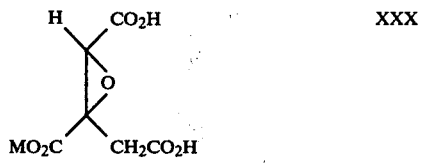

XXX wherein M is alkali metal, which is cleaved by the hereinbefore described methods to the chloroacid II.

While the mono-alkali metal salt of (±)-threo-epoxyaconitic acid is conveniently depicted as structural formula XXX, it is understood that the alkali metal may be associated with one of the two other carboxyl groups as shown in formulas XXXI and XXXII.

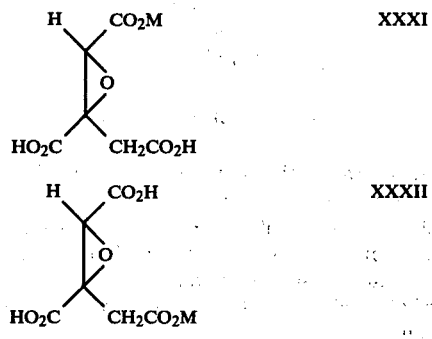

XXXI

XXXII wherein M is alkali metal.

The conversion of trans-aconitic acid (III) to the mono-alkali metal salt of (±)-threo-epoxyaconitic acid XXX may be accomplished by one of several processes. In the first, trans-aconitic acid (III) is transformed into the di-alkali metal salt of (±)-threo-chlorocitric acid, β-lactone (VI) as herein described. Instead of hydrolyzing the β-lactone VI directly to the chloroacid II under acidic conditions as herein disclosed, it has been found to be particularly efficacious to first hydrolyze the β-lactone function of VI and concomitantly displace the chloro function to the tri-alkali metal of (±)-threo-epoxyaconitic acid XXXIII

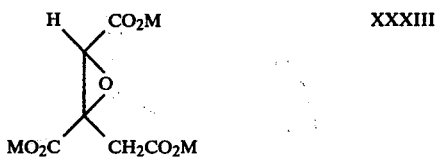

XXXIII wherein M is alkali metal, under alkaline conditions, then partially neutralize the tri-salt XXXIII to the mono-salt XXX and finally cleave the isolable mono-salt XXX to (±)-threo-chlorocitric acid II by, for example, sodium chloride in the presence of hydrochloric acid, according to the procedure reported herein.

The alkali induced hydrolysis-displacement of the dialkali metal salt of (±)-threo-chlorocitric acid, β-lactone (VI) is performed by treating the chlorination reaction mixture with an alkali metal hydroxide such as lithium, sodium or potassium hydroxide, preferably potassium hydroxide, while maintaining the reaction temperature between about 0° C. to about 40° C., more preferably at about 0° C. to 25° C.

The partial neutralization of the tri-salt XXXIII is accomplished by adjusting the pH of the hydrolysis-displacement reaction mixture to a value within the range of about 7.0 to 7.5, preferably to a value of about 7.2, cooling the resulting reaction mixture to a temperature preferably within the range of above −20° C. to 20° C., more preferably to a temperature of about 0° C. to 5° C., adding about two molar-equivalents of acid collecting the precipitate and purifying it by recrystallization from water or water-alkanol mixtures, such as water-methanol, water-ethanol and the like. Water is the preferred recrystallization solvent.

The pH is conveniently adjusted by adding a mineral or organic acid to the reaction mixture. Among mineral acids, there may be mentioned hydrohalic acids, such as hydrochloric acid, hydrobromine acid, nitric acid, sulfuric acid and perchloric acid and the like. Among organic acids there may be mentioned sulfonic acids such as methanesulfonic acid, benzenesulfonic acid and p-toluenesulfonic acid, trichloroacetic acid and trifluoroacetic acid. Mineral acids are preferred. Hydrohalic acids are more preferred. Hydrochloric acid is most preferred.

In the record process, trans-aconitic acid (III) is chlorohydrinated to the tri-alkali metal salt of (±)-threo-chlorocitric acid (XXXIV)

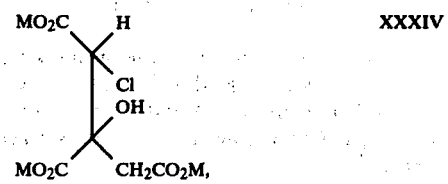

XXXIV wherein M is alkali metal, which is cyclized under alkaline conditions and partially neutralized under acidic conditions to the mono-alkali metral salt of (±)-epoxyaconitic acid (XXXIII).

The chlorohydrination is carried out by treating trans-aconitic acid (III) with an alkali metal hypochlorite, preferably potassium hypochlorite, preformed by the dissolution of chlorine in an alkali metal hydroxide solution, preferably, aqueous potassium hydroxide. While the chlorohydrination temperature is not narrowly critical, it is preferred to perform the reaction at a temperature within the range about −20° C. to about 25° C., more preferably at a temperature within the range of about −5° C. to 5° C., most preferably at a temperature of about 0° C. About two molar-equivalents of alkali metal hydroxide are initially employed to form the di-alkali metal salt of transaconitic acid (XXXV)

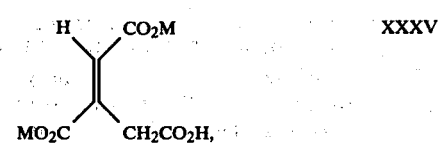

XXXV which may also be represented as the di-salts XXXVI and XXXVII.

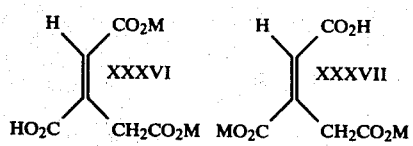

About two additional molar-equivalents of alkali metal hydroxide are subsequently employed to form sufficient alkali metal hypochlorite for the hypochlorination of di-salt XXXV.

The cyclization of the tri-alkali metal salt of (±)-threo-chlorocitric acid (XXXIV) to the tri-alkali metal salt of (±)-threo-epoxyaconitic acid (XXXIII) is accomplished by treating the chlorohydrination reaction mixture or the tri-alkali metal salt of (±)-threo-chlorocitric acid, dissolved in a suitable solvent, with an alkali metal hydroxide, preferably potassium hydroxide. The cyclization temperature is not narrowly critical. Nevertheless it is preferred to carry out the reaction at a temperature between about 15° C. to about 60° C., more preferably at a reaction temperature of about 25° C.

Suitable cyclization solvents include water and mixtures of water and lower alkanols such as methanol, ethanol and the like. Water is preferred.

The partial neutralization of the tri-alkali metal salt of (±)-trans-epoxyaconitic acid (XXXIII) is effected by treating it, or the reaction mixture in which it is derived, with a mineral or organic acid according to the hereinbefore described procedure for the related conversion of the di-alkali metal salt of (±)-threo-chlorocitric acid, β-lactam (VI).

In the third process, a variant of the second method, about two-thirds of a molar-equivalent of trans-aconitic acid is treated with about two molar-equivalents of an alkali metal hydroxide, preferably potassium hydroxide, in an appropriate solvent followed by about one molar-equivalent of preformed alkali metal hypochlorite, preferably potassium hypochlorite, and about one-third molar-equivalent of trans-aconitic acid to form (±)-threo-chlorocitric acid (XXXIV).

As appropriate solvent for the third process, there may be mentioned water and mixtures of water and lower alkanols such as methanol, ethanol and the like. Water is preferred.

While the hypochlorination temperature is not narrowly critical, it is preferable to perform the reaction at a temperature from about −20° C. to 10° C., more preferably at a temperature of about −10° C. to −5° C.

The (±)-threo-chlorocitric acid (XXXIV), so obtained by this variant, is transformed to the mono-alkali metal salt of (±)-threo-epoxyaconitic acid (XXX) by the methods hereinbefore described in the description of the first and second processes.

In the fourth process, (±)-threo-epoxyaconitic acid (XIII) is converted to the mono-alkali metal salt, preferably the mono-potassium salt, by treatment of the acid XIII with about one equivalent of an alkali metal hydroxide, preferably potassium hydroxide, in a suitable solvent such as water and mixtures of water and lower alkanols of the group consisting of methanol, ethanol, 2-propanol and the like. It is preferred to carry out the conversion of the tri-acid XIII to the mono-salt XIII at a reaction temperature of about 5° C., although the salt formation temperature is not critical. The mono-salt XIII so obtained, is isolated and purified as hereinbefore disclosed for the product of the other variants.

Alternatively, the reaction mixture in which (±)-threo-epoxyaconitic acid (XIII) is formed may be treated with about one equivalent of an alkali metal hydroxide, preferably potassium hydroxide, under the aforementioned conditions.

The mono-alkali metal salts of (±)-threo-epoxyaconitic acid (XXX) an generally isolated as the monohydrate.

(−)-threo-Chlorocitric acid (XV) may also be prepared from the mono-alkali metal salt XXX. In this alternative approach to optically active chloroacid XV, the salt is neutralized to (−)-threo-epoxyaconitic acid (XIII), which is in turn is resolved into (+)-threo-epoxyaconitic acid (XIV) via its bis (+)-p-nitro-α-methylbenzylamine salt XXXVIII

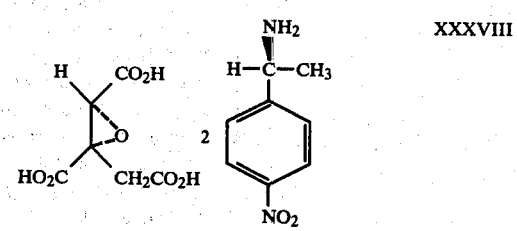

and cleaved into the chloroacid XV by methods well-known in the art or described hereinbefore.

The neutralization is conveniently performed by treating the mono-alkali metal salt XXX, preferably the mono-potassium salt, with a strong acid in an appropriate solvent. Among strong acids there may be mentioned mineral acid such as hydrochloric acid, hydrobromine acid, nitric acid, perchloric acid, sulfuric acid and so forth, and organic acids such as methanesulfonic acid, benzenesulfonic acid, p-toluenesulfonic acid, trifluoroacetic acid, trichloroacetic acid and so forth. Among appropriate solvents there may be mentioned water, lower alkanol such as methanol, ethanol, 2-propanol and the like, mixtures of water and lower alkanols, and ketones such as acetone, methylethyl ketone, diethylketone and the like. Mineral acids and ketones are preferred. Sulfuric acid and acetone are particularly preferred.

The chlorocitric acids of the present invention of formula I and the stereoisomers, optical antipodes and pharmaceutically acceptable salts thereof exhibit potent anorectic (appetite suppressant) activity in mammals and are thus useful in the treatment of obesity in such species. Of particular interest is (−)-threo-chlorocitric acid of formula XV and pharmaceutically acceptable salts thereof, which are significantly more active in the acute meal-fed assay utilizing three diets and in pyramiding dose studies as measured by reduction in food consumption than hydroxycitric acid, citric acid being inactive in these determinations.

Similarly, in both short- and long-term chronic studies, (−)-threo-chlorocitric acid suppressed appetite and reduced body weight gain in mammals more efficaciously than hydroxycitric acid or citric acid. Even though (−)-threo-chlorocitric acid, unlike hydroxycitric acid, is devoid of metabolic activity as an inhibitor of lipid and cholesterol syntheses, carcass analysis indicated that weight loss was due to reduction in body lipids.

While the mechanism of action of the chlorocitric acids of formula I of the present invention has not been conclusively established, it appears that the significant mode of action in producing anorexia is a delay in gastric emptying. At comparable doses, hydroxycitric acid also delayed gastric emptying. Contributory modes of action of hydroxycitric acid include, however, inhibition of fatty acid and cholesterol syntheses.

The chlorocitric acids of the present invention, useful in the treatment of obesity can be made up in the form of conventional pharmaceutical preparations containing, in addition to the active ingredients, carrier material. Such carrier material includes conventional organic or inorganic inert pharmaceutical adjuvants, additives and excipients suitable for parenteral or enteral administration such as, for example, water, gelatin, lactose, starch, magnesium stearate, talc, vegetable oil, gums or the like. They can be administered in conventional pharmaceutical forms, e.g., solid forms, for example, tablets, dragees, capsules, suppositories or the like; or in liquid forms, for example, suspensions or emulsions. Moreover, the pharmaceutical compositions containing compounds of this invention can be subjected to conventional pharmaceutical expedients such as sterilization, and can contain conventional pharmaceutical excipients such as preservatives, stabilizing agents, emulsifying agents, salts for the adjustment of osmotic pressure or buffers. The composition can also contain other therapeutically active materials.

A suitable pharmaceutical dosage unit can contain from about 10 to about 1000 mg of (—)-threo-chlorocitric acid or its isomers. Suitable parenteral and oral dosage regimens in mammals comprise from 1 mg/kg to about 150 mg/kg per day. However, for any particular subject, the specific dosage regimen should be adjusted according to individual need and the professional judgement of the person administering or supervising the administration of the aforesaid compounds. It is to be understood that the dosages set forth herein are exemplary only and that they do not to any extent, limit the scope or practice of this invention.

The chlorocitric acids of the present invention can also be compounded or blended with a feed additive, premix, feed concentrate or feed additive supplement to form a dietary admixture for administration to an animal. A feed additive, concentrate or premix is a composition to be diluted to produce a complete feed, i.e., a composition to be administered as a sole ration. A feed additive supplement is a composition to be consumed directly by the animal or which can be further diluted to produce a complete feed or which can be ingested and used as a supplement to other rations. Dietary admixtures usually contain a relatively large percentage of chlorocitric acids, i.e., the active ingredient, and are conveniently prepared by adding the active ingredient to a suitable carrier and mixing, so as to assume a substantially uniform dispersion of the anorectic in the carrier. Suitable carriers are solids that are inert with respect to the active ingredient and which may safely be ingested by the animals to be treated. Typical of such carriers are commercial animal feeds, ground cereal grains, grain by-products, plant protein concentrates (soy, peanuts, etc.), fermentation by-products, salt, limestone, inorganic compounds, and the like or mixtures thereof. Liquid dispersions can be prepared by using water or vegetable oil, preferably including a surface active agent, emulsifying agent, and the like in the liquid dispersion such as ethylenediamine tetraacetic acid, etc. and solubilizers. Any suitable carrier or extender material can function as the inert ingredient in the solid form of the antiobesity agent provided that it is inert to the active material and is non-toxic insofar as the animal to which it is to be administered is concerned.

The active ingredient may be blended into a mash, pellet or any desired configuration with the inert carrier or extender solid material by any convenient technique. For example, compositions can be formed by finely grinding or pulverizing the active ingredient and the inert ingredient using any commercially available grinder or pulverizer with or without the feed material being present. If the feed material is not present when the grinding or pulverizing is effected, the resultant material can be distributed, in accordance with the present invention, in any conveniently available feed material. Typical animal feeds which can be medicated with the active ingredient of this invention can contain several ingredients, for example, they can contain high energy grain products such as corn, wheat, wheat red dog flour, milo, oatmeal or the like; medium and low energy grain products such as oats, barley, wheat flour, middlings, standard middlings or the like; stabilized fats; vegetable protein such as soybean meal, corn gluten meal, peanut meal or the like; animal protein such as fish meal, fish solubles, meat scraps or the like; UGF (unidentified growth factor) sources and other B-vitamin carriers such as dried milk products, dried brewers yeast, distillers dried solubles, fermentation solubles, or the like; dehydrated alfalfa meal; and various special additives such as additional riboflavin, vitamin $B_{12}$, calcium pantothenate, niacin, choline, vitamin K and vitamin E or the like, as well as stabilized vitamin A, vitamin $D_3$ (D-activated animal sterols); calcium and phosphorus supplements such as dicalcium phosphate, steamed bone meal, defluorinated phosphate, limestone or the like; iodized salt, manganese sulfate, zinc carbonate, an antibiotic feed supplement, methionine or its hydroxy analog and an antioxidant.

As is evident from the above, the antiobesity compositions are intended for oral ingestion. They can be added to the normal feed supply of the treated animal or can be administered by other procedures, such as incorporating the same in a tablet, pill, or bolus and supplying it forcibly to the animal. The administration of the active ingredient must be considered in terms of the specific animal under the husbandry practices encountered.

The actual concentration of the active ingredient in animal feed can, of course, be adjusted to the individual needs and may vary over a wide range. The limiting criteria of the concentration are that the minimum concentration is such that a sufficient amount of active ingredient is provided to effect the desired reduction of obesity and the maximum concentration is such that the amount of composition ingested does not result in any untoward or undesirable side effects.

Thus, for example, a feed premix or complete feed contains sufficient active ingredient to provide from about 0.0025% to about 1.00% by weight of the daily feed consumption. Preferably, about 0.0625% to 0.40% by weight is used. Most preferably about 0.125% by weight is used.

The present invention may be more clearly illustrated by the following examples. All temperatures are stated in degrees Centigrade.

EXAMPLE 1

(±)-Threo-Chlorocitric acid

(a). Hypochlorination Method 174 g. (1.0 mole) of trans-aconitic acid was added portionwise to a stirred solution of 120 g. (3.0 mol) of sodium hydroxide in 400 ml. of water. Throughout the addition, the reaction temperature was maintained at ca. 25° by adding ice to the mixture as needed (total ca. 350 g.). When the acid had completely dissolved, the solution was at pH 7.5. (In other experiments, the solution was adjusted to pH 7.5 by the addition of either 2 N sodium hydroxide or trans-aconitic acid as needed.) The solution was then transferred to a 3-liter, 3-necked round bottom flask fitted with a mechanical stirrer, a gas inlet tube (fritted disc type), a thermometer and a gas outlet. The gas outlet was connected via rubber tubing to a Pasteur pipette which was partially submerged in a column of water in a graduated cylinder. This was used to monitor the rate of gases escaping the reaction vessel. The reaction mixture was cooled to 5° and purged with argon. Chlorine gas was then added to the rapidly stirred mixture as fast as it could be consumed without excess gas exiting the gas outlet. Initially the temperature rose rapidly to ca. 15° but it was maintained at 10°-15° throughout the reaction by external cooling (ice-acetone bath). After 20-30 minutes, the absorption rate of chlorine gas diminished rapidly and the solution became typically green. When no more gas was absorbed (as indicated by the gas exit flow) the addition of chlorine gas was stopped and the mixture was stirred at 10° for another 10 minutes. Excess chlorine gas was then purged by bubbling argon gas through the reaction mixture.

b. Epoxide Cleavage Method

To a solution of 123 g (0.5 mol) of mono-potassium (±)-threo-epoxyaconitic acid, monohydrate, 28 g (0.375 mol) of potassium chloride and 120 ml of water was added 88 ml (ca. 1.06 mol) of conc hydrochloric acid. The reaction mixture was heated at 70° for 15 hours, allowed to cool to room temperature and concentrated at 50° and 0.5 to 1.0 mm of mercury. Ethyl acetate (250 ml) was added and the mixture was agitated at 40°. The precipitated potassium chloride was collected and washed with 350 ml portion of ethyl acetate. The filtrate was evaporated to dryness at 50° under water aspirator pressure. The residue was dissolved in ethyl acetate, treated with anhydrous magnesium sulfate and filtered through a pad of Celite Filter-Aid. The filter cake was washed with ethyl acetate. Carbon tetrachloride was added to the filtrate, with stirring, until the cloud point was reached. The turbid mixture was seeded with authentic crystalline (±)-threo-chlorocitric acid, monohydrate, and the mixture was stirred for 2 hours at room temperature and allowed to stand for 16 hours in a refrigerator. The precipitate was collected, washed with carbon tetrachloride, ethyl acetate (3:1) and air dried to afford 70.9 g of product, m.p. 74°-76°, having a neutralization equivalent of 81.58 of g/equiv (theoretical neutralization equiv 81.52).

The mother liquors were evaporated to dryness at 50° and water aspirator pressure. The residue was dissolved in 125 ml of ethyl acetate and treated with carbon tetrachloride as described above to give 20.7 g of product, m.p. 74°-76°, having a neutralization equivalent of 82.00.

A 91.0 g-portion of the combined first and second crops of the product was dissolved in 250 ml of ethyl acetate and treated with ca. 500 ml of carbon tetrachloride. The turbid solution was seeded with crystalline (±)-threo-chlorocitric acid monohydrate and stored in a refrigerator overnight. The precipitate was collected, washed with carbon tetrachloride and ethyl acetate as described above and air dried to yield 84.3 g of purified product, m.p. 74°-76°, having a neutralization equivalent of 81.5.

Calcd for $C_6H_7ClO_7.H_2O$: C, 29.46; H, 3.71; Cl, 14.50; $H_2O$, 7.36; Found: C, 29.27; H, 3.72; Cl, 14.23; $H_2O$, 7.43.

The reaction was then acidified using 175 ml conc. hydrochloric acid (2.1 mol) and then it was heated at 70° for 1 hour to hydrolyze the $\beta$-lactone. The solution was then concentrated in vacuo to dryness and the residue was triturated with warm ethyl acetate (3×500 ml). The combined extracts were filtered to remove residual sodium chloride and then were dried over magnesium sulfate. Evaporation of the solvent gave a solid which was redissolved in ethyl acetate (500 ml) and the solution was diluted to the cloud point with carbon tetrachloride. After the mixture was stirred overnight at room temperature, the solid which had formed was recovered by filtration to give 102.0 g of (±)-threo-chlorocitric acid (dried in vacuo to constant weight), mp 96°-101°; neutralization equivalent 75.81 g/eg (Theory 75.52 g/eg).

The mother liquors were concentrated to dryness and were then crystallized as above to give an addition 60.7 g of pure (±)-threo-chlorocitric acid.

The analytically pure material was obtained by recrystallization from ethyl acetate-carbon tetrachloride and had mp 76°-77° as the monohydrate.

EXAMPLE 2

(±)-erythro-Chlorocitric acid 74.0 g of cis-aconitic anhydride (0.474 mol) was dissolved in 200 ml of water containing 100 g ice. A solution of sodium hydroxide (46.25 g; 1.15 mol) in 100 ml of water was added slowly with stirring. The reaction temperature was held below 20° by the simultaneous addition of 200 g ice. When the base addition was completed, 15.25 g sodium tungstate dihydrate, followed by 55.5 ml of 30% hydrogen peroxide was added to the mixture. The oxidation was initiated by gently warming the stirred solution to 23°. The external heat source was then removed whereupon the heat of reaction caused the mixture temperature to slowly climb to 51.5° over 25 minutes after which it started to decline. After stirring an additional 7-10 minutes, the reaction mixture was treated with 150 ml conc hydrochloric acid and 150 g sodium chloride and heated at 75° for 15 minutes. In this way the intermediate (±)-erythro-epoxyaconitic acid was converted in situ to (±)-erythro-chlorocitric acid. After the reaction mixture was cooled to room temperature, 2.3 g sodium bisulfite₃ was added to destroy residual hydrogen peroxide. The solution was then transferred to a liquid-liquid extraction apparatus and was continuously extracted using ether.

The first extract collected after 21 hours was dried over magnesium sulfate and concentrated in vacuo to give 73.0 g of solid crude chlorocitric acid contaminated with ca 8% trans-aconitic acid. Crystallization of this material twice from ethyl acetatecarbon tetrachloride furnished essentially pure (±)-erythro-chlorocitric acid, mp 162°–164°.

A second extract collected after an additional 48 hrs was worked up as above to give an additional 18.5 g of the chlorocitric acid, mp 163°–165°.

EXAMPLE 3

(±)-threo-Chlorocitric acid, β-lactone

A solution of trisodium trans-aconitate prepared from 58.0 g trans-aconitic acid (0.33 mol) and sodium hydroxide (40 g; 1.0 mol) in 300 ml of water was cooled to 5° and chlorinated as in Example 1. The resulting solution of disodium chlorocitric acid, β-lactone was purged free of excess chlorine gas and then was treated with 60 ml 12 N hydrochloricacid (0.72 equiv). The reaction mixture was extracted (3 times) with ethyl acetate and the extracts were combined and dried over magnesium sulfate. The ethyl acetate solution was then concentrated in vacuo to ca 200 ml and was diluted to the cloud point with carbon tetrachloride. The resulting crystalline material was collected by filtration to give a total of 41.5 g of pure (±)-threo-chlorocitric acid, β-lactone, mp 162°–164°.

EXAMPLE 4

Resolution of (±)-erythro-chlorocitric acid 30 g of (±)-erythro-chlorocitric acid (132.4 mmol) was dissolved in 175 ml of a methanol-water mixture (49:1). The solution was cooled to 15° and 39.5 g (−)-p-nitro-α-methyl-benzylamine (238 mmol) in 75 ml of the same methanol-water mixture was added over 2–3 minutes. The mixture was stirred at room temperature for 18 hours during which time a white solid formed. The solids were collected by filtration and then were washed with ethanol and with ether to give 24.0 g of partially resolved (+)-erythro-chlorocitric acid, bis(−)-p-nitro-α-methylbenzylamine salt. Attempts to further purify this salt by normal recrystallization procedures were frustrated by the heat required to dissolve the salt. This caused extensive conversion to the corresponding erythrohydroxycitric acid.

The impure salt was then split in the following manner: hydrogen chloride gas was bubbled through a stirred suspension of finely divided salt (27.1 g) in ether for 30 minutes. The resulting solid (−)-p-nitro-α-methylbenzylamine hydrochloride (19.9 g, mp 247°–249°) was removed by filtration and the filtrate was concentrated in vacuo to give 10.9 g of partially resolved (+)-erythro-chlorocitric acid as an oil (ca 65% optical purity). The crude chlorocitric acid was treated with diazomethane and the resulting trimethyl chlorocitrate was analyzed by nuclear magnetic resonance spectroscopy using chiral shift reagents to determine optical purity.

The recovered (−)-p-nitro-α-methylbenzylamine hydrochloride salt was partitioned between dichloromethane and 1 N sodium hydroxide. The amine recovered from this process (15.6 g) in 40 ml methanol-water (49:1) was added to a solution of the crude (+)-erythro-chlorocitric acid in 40 ml methanol-water (49:1) and the mixture, after stirring several hours, deposited 18.1 g of enriched bis-amine chlorocitrate salt.

The salt was again split using ethereal hydrogen chloride and was then reformed in the manner described above. This gave 14.4 g of the bis-amine chlorocitric acid. The (+)-erythro-chlorocitric acid recovered from the latest salt was recrystallized from ethyl acetate-carbon tetrachloride to give 4.3 g of material (29% chemical yield) which was 85% optically pure.

The mother liquors of the solution of the partially resolved (+)-erythro-chlorocitric acid, bis-(−)-p-nitro-α-methylbenzylamine salt were treated with 13 ml (0.52 mol) of conc hydrochloric acid and evaporated to dryness. 1,2-Dimethoxyethane was added and the solution was evaporated to dryness. Ether was added to the residue, the mixture was stirred and the precipitate was collected to afford 29.2 g of (−)-p-nitro-α-methylbenzylamine hydrochloride.

The filtrate was concentrated to dryness and the residue, rich in (−)-erythro-chlorocitric acid, was dissolved in 90 ml of methanol-water (49:1). A solution of 25.3 g (0.125 mol) of (+)-p-nitro-α-methylbenzylamine and 50 ml of methanol-water (49:1) was added. The resulting mixture was stirred at room temperature for 20 hours and the precipitate was collected to afford 15.0 g of bis-(+)-p-nitro-α-methylbanzylamine salt enriched in (−)-erythro-chlorocitric acid. The salt was suspended in 185 ml of ether and hydrogen chloride was added to the suspension over a period of 30 min. The precipitated (+)-p-nitro-α-methylbenzylamine hydrochloride (10.7 g) was collected on a filter. The filtrate was concentrated to dryness and the residue was dissolved in 40 ml of methanol-water (49:1). To the methanol-water solution was added a solution of 8.9 g (0.54 mol) of (+)-p-nitro-α-methylbenzylamine and 15 ml of methanol-water (49:1) and the solution was stirred at room temperature for ca. 2.5 hours. The precipitate, (11.75) enriched in (−)-erythro-chlorocitric acid bis-(+)-p-nitro-α-methylbenzylamine salt, was suspended in ether and the resulting suspension was saturated with hydrogen chloride. The precipitated (+)-p-nitro-α-methylbenzylamine hydrochloride (8.09 g) was collected and the filtrate was concentrated. Recrystallization of the residue from ethyl acetate-carbon tetrachloride gave 3.9 g of (−)-erythro-chlorocitric acid (85% optical purity).

EXAMPLE 5

(−)-threo-Chlorocitric acid 105 g (0.5 mol) (+)-threo-epoxyaconitic acid monohydrate was dissolved in 150 ml of water containing 43 ml (0.516 mol) conc hydrochloric acid. Sodium chloride (50 g) was added to the stirred solution and the mixture was heated at 70° for 12 hours. The solution was then evaporated to dryness in vacuo (ca 1 mm; 50°) and the residue was triturated with 400 ml warm ethyl acetate. The mixture was filtered free of sodium chloride and the filtrate was decolorized (acid washed charcoal), dried over magnesium sulfate and concentrated in vacuo to a crystalline mass. The residue was dissolved in 250 ml ethyl acetate and the solution was brought to a cloud point using carbon tetrachloride. The mixture was stirred several hours at room temperature and then was chilled in a refrigerator overnight. The solids were removed by filtration to give 68.5 g of (−)-threo-chlorocitric acid, mp 138°–140°[α]$_D^{25}$ −6.60° (c, 2.0, H$_2$O). An additional 20.2 g of material [mp 138°–140° ; [α]$_D^{25}$ −6.6°] were recovered from the mother liquors.

The analytically pure specimen was obtained by recrystallization from ethyl acetate-carbon tetrachloride, mp 140.5°–142.0° ;[α]$_{25}^D$ −7.05° (c, 2.0, H$_2$O).

EXAMPLE 6

(+)-threo-Chlorocitric acid (−)-threo-Epoxyaconitic acid monohydrate (105 g, 0.5 mol) was dissolved in 150 ml of water containing 43.0 ml conc. hydrochloric acid (0.516 mol). To the stirred solution 50 g of sodium chloride was added and the mixture was heated at 70° for 12 hours. The reaction was worked up as in example 5 to give (+)-threo-chlorocitric acid in two crops:

Crop #1: mp 138°–140°;$[\alpha]_D^{25}+6.65°$ (C, 2.0, $H_2O$); 55.2 g.

Crop #2: mp 138°–140°;$[\alpha]_D^{25}+6.55°$ (C, 2.0, $H_2O$); 23.0 g.

Recrystallization of the solid from ethyl acetate-carbon tetrachloride gave the analytically pure material, mp 140.5°–142°;$[\alpha]_D^{25}+6.9°$ (C, 2.0, $H_2O$).

EXAMPLE 7

(−)-erythro-Epoxyaconitic acid

A solution of 49.2 g (−)-threo-1-mesyloxy-2-hydroxy-1,2,3-propanetricarboxylic acid, trimethyl ester (0.15 mole) in 340 ml acetic acid containing 170 ml conc hydrochloric acid was heated at 80° for 23 hours. The solvents were removed in vacuo and the crude product (mostly 1-mesyloxy-2-hydroxy-2-carbomethoxy-1,3-propanedicarboxylic acid) was evaporated several times from glyme to eliminate remaining acetic acid and hydrochloric acid. The residue was dissolved in 50 ml of water and the solution was added at a rapid dropwise rate with stirring to 157.5 ml of sodium hydroxide (0.63 mol) initially cooled to 5° (the temperature rose to ca 27° during the addition). The reaction was stirred at room temperature for 30 minutes to ensure complete hydrolysis of the remaining ester function as well as formation of the oxirane ring. The reaction mixture was cooled to 10° and then was adjusted to pH 7.5 using a total of 5.5 ml 3.6 N sulfuric acid, whereupon 12.5 ml of conc. sulfuric acid (0.45 eg) was added carefully to convert the trisodium epoxyaconitic acid into its free acid. The solution was concentrated in vacuo at ca. 30° until crystals of sodium sulfate decahydrate began to deposit and then it was diluted with 300 ml acetone. The inorganic salt was removed by filtration and the filtrate was evaporated to dryness under reduced pressure. A solution of the reaction product in tetrahydrofuran (300 ml) was filtered to remove residual sodium sulfate, dried over magnesium sulfate, decolorized (Norit SG acid washed charcoal) and concentrated to dryness in vacuo to give a solid residue. Crystallization of the crude product from ethyl acetate-carbon tetrachloride (400:300 ml) furnished 17.7 g of (−)-erythro-epoxyaconitic acid, mp 169°–172°. This sample was contaminated by a minor amount of sodium methylsulfonate which was removed by placing the material in a thimble in a Sohxlet apparatus and extracting it using ether (1.5 l) over 1.5 hours. The ether extract was concentrated in vacuo and the solid residue was recrystallized from ethyl acetate-carbon tetrachloride (325:125 ml) to give 13.0 g of pure (−)-erythro-epoxyaconitic acid mp 179.5°–181°;$[\alpha]_D^{25}-52.4°$ (C, 1.0, $H_2O$). Concentration of the mother liquor afforded a second crop, 2.1 g; mp 179°–181°.

EXAMPLE 8

(+)-erythro-Epoxyaconitic acid

Using the procedure described in Example 7,112.7 g (+)-threo-1-mesyloxy-2-hydroxy-1,2,3-propanetricarboxylic acid, trimethyl ester was converted into 36.2 g (+)-erythro-epoxyaconitic acid, mp 173°–175°. This material was again contaminated with a trace of sodium methanesulfonate which was removed as before to give the analytically pure epoxy triacid, mp 179.5°–181°;$[\alpha]_D^{25}+52.6°$ (C, 1.0, $H_2O$).

EXAMPLE 9

(−)-erythro-Chlorocitric acid

A solution of 8.1 g (+)-erythro-epoxyaconitic acid (42.6 mmol) in 43 ml 1 N hydrochloric acid (43 mmol) containing 15 g sodium chloride was heated at 78° for 25 minutes. At the end of this time, examination of the reaction mixture by nuclear magnetic resonance spectroscopy showed a significant amount of starting epoxide remaining and so the reaction was heated an additional 20 minutes at 80° to complete the reaction. Evaporation of the solvent in vacuo left a residue consisting of crude (−)-erythro-chlorotric acid and sodium chloride. The organic material was dissolved in glyme and the resulting solution was filtered to remove sodium chloride and then was dried over magnesium sulfate and concentrated under reduced pressure. Crystallization of the crude reaction product from ethyl acetate-carbon tetrachloride afforded 7.4 g of essentially pure (−)-erythro-chlorocitric acid. Recrystallization furnished 5.4 g (dried to constant weight) of pure triacid, mp 133.5°–135°;$[\alpha]_D^{25}-2.2°$ (C, 2.0, $H_2O$).

EXAMPLE 10

(+)-erythro-Chlorocitric acid (−)-erythro-Epoxyaconitic acid (9.5 g) was converted into 7.6 g of (+)-erythro-chlorocitric acid (mp 132°–134°) by a procedure essentially identical to that described in Example 9. Recrystallization of the chlorocitric acid thus obtained afforded 5.3 g of analytically pure material, mp 133.5°–135°;$[\alpha]_D^{25}+2.2°$ (C, 2.0, $H_2O$).

EXAMPLE 11

(±)-threo-Epoxyaconitic acid trans-Aconitic acid (87.0 g, 0.5 mol) was added portionwise to a solution of 60.0 g of sodium hydroxide (1.5 mol) in 200 ml of water. 150 g of ice was added as needed to moderate the heat of neutralization. The mixture was cooled to 0°–5° and was chlorinated as in Example 1. The resulting solution of (±)-threo-chlorocitric acid, lactone disodium salt (purged free of excess chlorine gas) was cooled to −10° and then was treated with 40.0 g (1.0 mol) sodium hydroxide. The solution was stirred rapidly as the pellets dissolved and the reaction temperature was moderated by external cooling so that it did not exceed 20°. The mixture was stirred at 20° for 20 minutes and then 42 ml of conc sulfuric acid (1.512 equiv) was added dropwise with cooling. The solution was transferred to a liquid-liquid extractor and was extraced over 2–3 days using diethyl ether. The ether extract was dried over magnesium sulfate and concentrated in vacuo. The resulting solid was crystallized from ethyl acetate-carbon tetrachloride to give 67.8 g of (±)-threo-epxoy acid, mp 169°–172°. A second crop (8.85; mp 167°–170°) was collected from the mother liquors.

EXAMPLE 12

(−)-threo-Hydroxycitric acid (−)-threo-Hydroxycitric acid ethylenediamine salt (26.8 g, 0.1 mole) was added in one portion to a stirred mixture of trifluoroacetic acid (130 ml) and water (5.0 ml) previously cooled to 5°–10°. Within several minutes the salt had essentially all dissolved and crystals of (−)-threo-hydroxycitric acid had begun to form in the mixture. After 30 minutes the solids were collected by filtration and were washed with trifluoroacetic acid (3×50 ml). The mother liquors were discarded and the solid was washed with ether and dried to give 20.1 g of the triacid, mp 154.5°–155.5°. This material was recrystallized by dissolving 20.1 g of triacid in 18 ml of water at 15° and diluting the solution in one portion with 100 ml trifluoroacetic acid. The mixture was chilled to −10° in an acetone ice bath and the resulting crystalline material was recovered to give 19.2 g of (−)-threohydroxycitric acid, mp 156.5°–158°; $[\alpha]_D^{25} -9.9°$ (C, 1.0, $H_2O$).

EXAMPLE 13

COMPARATIVE ANORECTIC ACTIVITY OF (±)-threo-CHLOROCITRIC ACID AND TRISODIUM (−)-threo-HYDROXYCITRIC ACID Charles River female rats (Charles River Breeding Laboratories, Wilmington, Mass.), weighing 150 to 175 g, were individually housed in wire-bottomed cages in a temperature-regulated (22° C.) light-controlled room (12 hr light, 6 a.m. to 6 p.m. and 12 hr dark, 6 p.m. to 6 a.m.). Animals were fasted 48 hr, then meal-fed the 70% glucose diet described by A. C. Sullivan, et al., J. Nutrition, 101, 265 (1971) from 8 to 11 a.m. Following 5 to 13 days alimentation on the meal-feeding regimen, rats were dosed with the appropriate compounds orally by intubation ½ hr before the 3 hr meal. Food cups were weighed immediately after the meal. The control group consists of 31 rats while each drug treated group consists of 5 to 12 rats.

The G-70 diet consisted of 70% glucose, 23% vitamin-free casein, 5% Phillips and Hart salt mixture IV, 1% corn oil, 1% complete vitamin mixture, and 40 g/kg cellulose. To ensure complete uniformity, all diets were mixed with a twen-shell dry blender equipped with an itensifier bar (Patterson-Kelley Co., East Stroudsburg, Pa.).

| | RESULTS | | | |
|---|---|---|---|---|
| | Food Consumption | | | |
| | (±)-threo-Chlorocitric Acid | | Trisodium (−)-threo-hydroxycitrate | |
| Concentration[a] mmoles/kg body weight | g | % of control | g | % of control |
| Control | 11.2 ± 0.5[b] | 100 | 11.2 ± 0.5 | 100 |
| 2.63 | 3.8 ± 0.3** | 34 | 8.9 ± 0.8** | 79 |
| 1.32 | 3.1 ± 0.4** | 28 | 9.9 ± 1.0 | 88 |
| 0.66 | 3.9 ± 0.3** | 35 | 9.0 ± 0.6** | 80 |
| 0.33 | 5.7 ± 0.5** | 51 | 11.5 ± 0.7 | 103 |
| 0.17 | 6.8 ± 0.7** | 61 | | |
| 0.08 | 6.4 ± 0.6** | 57 | | |

[a]Compounds were dissolved in water and administered orally at the indicated concentrations.
[b]Each value is the mean ± S.E.
**$p \leq 0.01$

EXAMPLE 14

EFFECT OF STEREOISOMERS OF CHLOROCITRIC ACID ON FOOD CONSUMPTION

Charles River female rats (Charles River Breeding Laboratories, Wilmington, Mass.), weighing 130 to 150 g, were individually housed in wire-bottomed cages in a temperature-regulated (22° C.) light-controlled room (12 hr light, 6 a.m. to 6 p.m. and 12 hr dark, 6 p.m. to 6 a.m.). Animals were fasted 48 hr, then meal-fed the 70% glucose diet described by A. C. Sullivan, et al., J. Nutrition, 101, 265 (1971) from 8 to 11 a.m. Following 5 to 12 days alimentation on the meal-feeding regimen, rats were dosed with the appropriate compounds orally by intubation ½ hr before the 3 hr meal. Food cups were weighed immediately after the meal. The control group consisted of 5 to 10 rats, while the experimental group consisted of 4 to 6 rats.

| | RESULTS | | | |
|---|---|---|---|---|
| | Food Consumption | | | |
| | 2.63 mmoles/kg body weight | | 0.66 mmoles/kg body weight | |
| Treatment | g | % of control | g | % of control |
| Control | 13.5 ± 0.8[a] | 100 | 8.2 ± 1.2 | 100 |
| Citric Acid | 12.7 ± 1.7 | 94 | — | — |
| (+)-threo-Chlorocitric acid | 5.1 ± 1.2*** | 38 | 6.8 ± 1.0 | 83 |
| (−)-threo-Chlorocitric acid | 2.2 ± 0.5*** | 16 | 4.8 ± 0.7* | 59 |
| (−)-erythro-Chlorocitric acid | 7.2 ± 1.5*** | 53 | 7.0 ± 1.9 | 85 |
| (+)-erythro-Chlorocitric acid | 10.5 ± 0.8* | 78 | 8.1 ± 1.6 | 99 |

[a]Each value is the mean ± S.E.
*$p \leq 0.05$
***$p \leq 0.001$

EXAMPLE 15

THE EFFECT OF (+)-threo-CHLOROCITRIC ACID AND (−)-threo-CHLOROCITRIC ACID ON FOOD CONSUMPTION OF THREE DIETS Charles River female rats (Charles River Breeding Laboratories, Wilmington, Mass.), weighing 170 to 200 g, were individually housed in wire-bottomed cages in a temperature-regulated (22° C.) light-controlled room (12 hr light, 6 a.m. to 6 p.m. and 12 hr dark, 6 p.m. to 6 a.m.). Animals were fasted 48 hr, then meal-fed the indicated diets from 8 to 11 a.m. Following 5 to 12 days alimentation on the meal-feeding regimen, rats were dosed with the appropriate compounds orally by intubation ½ hr before the 3 hr meal. Food cups were weighed immediately after the 1st, 2nd and 3rd hr of the meal. The control groups consisted of 8 to 10 rats and the experimental group considered of 5 to 6 rats.

| Treatment | Diet | Dose mmoles (mg)/kg | Food Intake (g)[a] 1st hr | 2nd hr | 3rd hr | Total |
|---|---|---|---|---|---|---|
| Control | 70% Glucose | — | 5.8 ± 0.7[b] | 4.8 ± 0.5 | 1.9 ± 0.5 | 12.6 ± 1.2 |
| (+)-threo-Chlorocitric acid | 70% Glucose | 0.66 (150) | 3.2 ± 0.5* | 5.1 ± 1.3 | 1.7 ± 0.3 | 10.1 ± 1.7 |
|  | 70% Glucose | 0.33 (75) | 6.2 ± 1.8 | 2.4 ± 0.8* | 2.4 ± 0.5 | 11.0 ± 2.3 |
| (−)-threo-Chlorocitric acid | 70% Glucose | 0.66 (150) | 2.7 ± 0.4* | 1.7 ± 0.3* | 2.3 ± 0.5 | 6.7 ± 0.7** |
|  | 70% Glucose | 0.33 (75) | 2.2 ± 0.5** | 2.2 ± 0.5** | 3.8 ± 0.4* | 8.2 ± 1.1* |
| Control | Chow | — | 7.7 ± 0.7 | 3.0 ± 0.5 | 3.5 ± 0.5 | 14.1 ± 0.9 |
| (+)-threo-Chlorocitric acid | Chow | 0.66 (150) | 7.7 ± 0.5 | 3.9 ± 0.5 | 1.8 ± 0.9 | 13.4 ± 0.9 |
|  | Chow | 0.33 (75) | 7.4 ± 0.6 | 2.6 ± 0.7 | 2.2 ± 0.5 | 12.2 ± 0.4 |
| (−)-threo-Chlorocitric acid | Chow | 0.66 (150) | 3.6 ± 0.9** | 1.4 ± 0.2* | 1.9 ± 0.4* | 6.9 ± 1.2** |
|  | Chow | 0.33 (75) | 4.2 ± 1.4* | 1.6 ± 0.4 | 2.3 ± 0.7 | 8.1 ± 2.1* |
| Control | 20% Corn Oil | — | 6.8 ± 1.0 | 3.1 ± 0.7 | 2.9 ± 0.8 | 12.7 ± 0.7 |
| (+)-threo-Chlorocitric acid | 20% Corn Oil | 0.66 (150) | 6.7 ± 1.6 | 3.1 ± 0.6 | 2.2 ± 0.7 | 12.3 ± 1.6 |
|  | 20% Corn Oil | 0.33 (75) | 7.1 ± 1.2 | 3.9 ± 0.5 | 3.2 ± 0.6 | 14.2 ± 1.2 |
| (−)-threo-Chlorocitric acid | 20% Corn Oil | 0.66 (150) | 3.6 ± 0.6* | 2.2 ± 0.4 | 1.3 ± 0.4 | 7.1 ± 0.9* |
|  | 20% Corn Oil | 0.33 (75) | 4.0 ± 0.6 | 1.6 ± 1.1 | 1.3 ± 0.5 | 6.8 ± 1.6** |

[a] Food consumption was measured by weighing food cups at the indicated times, following the initiation of the meal.
[b] Each value is the mean ± S.E.
*P ≤ 0.05
**P ≤ 0.01

EXAMPLE 16

ANORECTIC ACTIVITIES OF STEREOISOMERS OF CHLOROCITRIC ACID

Charles River female rats (Charles River Breeding Laboratories, Wilmington, Mass.), weighing 196 to 210 g, were individually housed in wire-bottomed cages in a temperature-regulated (22° C.) light-controlled room (12 hr light, 6 a.m. to 6 p.m. and 12 hr dark, 6 p.m. to 6 a.m.). Animals were fasted 48 hr, then meal-fed a 70% glucose diet from 8 to 11 a.m. Following 5 to 12 days alimentation on the meal-feeding regimen, rats were dosed with the appropriate compounds orally by intubation ½ hr before the 3 hr meal for 3 days. The total food consumption and body weight gained during the 3 day period were determined. The control group consisted of 16 rats, while the experimental group consists of 8 rats.

EXAMPLE 17

ANORETIC EFFECT OF (±)-threo-CHLOROCITRIC ACID, (−)-threo CHLOROCITRIC ACID and (+)-threo-CHLOROCITRIC ACID IN 8 HOUR MEAL-FED ZUCKER RATS Lean (Fa/−) Zucker rats and obese (fa/fa) Zucker rats of both sexes were individually housed in wire-bottomed cages in a temperature-regulated (22° C.) light-controlled room (12 hr light, 6 a.m. to 6 p.m. and 12 hr dark, 6 p.m. to 6 a.m.). The animals were fed a high carbohydrate (70% glucose) diet ad libitum for 13 days, dosed with the indicated compounds by oral intubation for 9 days and allowed to recover for 3 days. The animals were then meal fed from 8 a.m. to 4 p.m. for a period of 5 days, following which they were continued on the same meal schedule for an additional 6 days.

| Treatment | Dose mmoles/kg | 3-Day Food Consumption g | % of control | 3-Day Body Weight Gain g | % of initial body weight |
|---|---|---|---|---|---|
| Control | — | 28.6 ± 1.1[a] | 100 | −0.2 ± 1.1 | −0.1 |
| (+)-threo-Chlorocitric acid | 1.32 | 26.5 ± 1.3 | 93 | −3.5 ± 1.2 | −1.7 |
| (−)-threo-Chlorocitric acid | 1.32 | 10.5 ± 1.3** | 37 | −22.4 ± 2.3** | −11.0 |
| (−)-erythro-Chlorocitric acid | 1.32 | 24.5 ± 1.8* | 86 | −4.8 ± 3.2 | −2.4 |
| (+)-erythro-Chlorocitric acid | 1.32 | 31.8 ± 2.3 | 111 | −1.5 ± 2.3 | −0.7 |

[a] Each value is the mean ± S.E.
*P ≤ 0.05
**P ≤ 0.01

During the 6-day period, the animals were administered the indicated compounds by oral intubation at 8 a.m. and 12 p.m. Food cups were weighed immediately after the meal.

| Treatment | Genotype[a] | Concentration mmoles/kg body weight | RESULTS Daily Food Consumption (g) Pretreatment 0 | Treatment Period (days) 1 | 2 | 3 | 4 | 5 | 6 |
|---|---|---|---|---|---|---|---|---|---|
| Control | Fa/— | — | 10.9 ± 0.6[b] | 10.6 ± 1.2 | 11.2 ± 1.0 | 12.5 ± 0.7 | 11.7 ± 1.0 | 13.4 ± 0.8 | 14.2 ± 1.3 |
| Citric Acid | Fa/— | 1.32 | 11.0 ± 0.8 | 10.6 ± 1.2 | 10.0 ± 1.2 | 12.7 ± 1.0 | 11.9 ± 0.7 | 12.6 ± 0.8 | 13.1 ± 0.9 |
| (±)-threo-Chlorocitric acid | Fa/— | 1.32 | 12.3 ± 0.7 | 11.6 ± 0.8 | 7.5 ± 0.8** | 8.6 ± 1.3** | 6.9 ± 1.0** | 6.1 ± 0.7** | 7.2 ± 1.0** |
| (−)-threo- | Fa/— | 0.66 | 10.8 ± 1.0 | 12.5 ± 1.1 | 7.0 ± 0.9** | 7.2 ± 0.7** | 5.4 ± 1.1** | 7.3 ± 1.5** | 7.5 ± 1.3** |

RESULTS -continued

| Treatment | Geno-type[a] | Concentration mmoles/kg body weight | Daily Food Consumption (g) Pretreatment 0 | Treatment Period (days) 1 | 2 | 3 | 4 | 5 | 6 |
|---|---|---|---|---|---|---|---|---|---|
| Chlorocitric acid | | | | | | | | | |
| (+)-threo-Chlorocitric acid | Fa/— | 0.66 | 10.6 ± 0.8 | 10.1 ± 0.8 | 8.7 ± 0.3** | 11.7 ± 0.7 | 9.8 ± 0.9 | 12.8 ± 0.9 | 11.4 ± 0.7 |
| Control | fa/fa | — | 11.1 ± 0.9 | 10.6 ± 0.5 | 12.4 ± 0.9 | 14.3 ± 1.3 | 12.4 ± 1.1 | 13.2 ± 0.7 | 14.3 ± 1.2 |
| Citric Acid | fa/fa | 1.32 | 13.4 ± 0.8 | 11.4 ± 0.8 | 13.8 ± 1.2 | 16.5 ± 1.0 | 14.8 ± 0.9 | 15.7 ± 1.2 | 16.0 ± 1.0 |
| (+)-threo-Chlorocitric acid | fa/fa | 1.32 | 14.3 ± 0.8** | 13.1 ± 0.9** | 7.8 ± 0.8** | 6.6 ± 0.2** | 5.9 ± 0.8** | 4.6 ± 1.1** | 5.3 ± 1.3** |
| (−)-threo-Chlorocitric acid | fa/fa | 0.66 | 13.1 ± 1.1 | 10.7 ± 0.7 | 5.9 ± 1.5** | 5.8 ± 0.9** | 5.5 ± 0.9** | 4.9 ± 1.0** | 5.1 ± 1.1** |
| (+)-threo-Chlorocitric acid | fa/fa | 0.66 | 14.3 ± 1.4 | 10.3 ± 0.4 | 8.8 ± 0.8** | 11.3 ± 1.0 | 11.6 ± 1.2 | 12.3 ± 1.5 | 14.2 ± 1.3 |

[a]Fa/—, lean rats; fa/fa, obese rats.
[b]Each value is the mean ± S.E.
*P ≤ 0.01

EXAMPLE 18

EFFECT OF (±)-threo-CHLOROOCITRIC ACID, (−)-threo-CHLOROCITRIC ACID and (+)-threo-CHLOROCITRIC ACID ON BODY WEIGHT GAIN IN 8 HOUR MEAL FED ZUCKER RATS Lean (Fa/—) Zucker rats and obese (fa/fa) Zucker rats of both sexes were individually housed in wire-bottomed cages in a temperature-regulated (22° C.) light-controlled room (12 hr light, 6 a.m. to 6 p.m. and 12 hr dark, 6 p.m. to 6 a.m.). The animals were fed a high carbohydrate (70% glucose) diet ad libitum for 13 days, dosed with the indicated compounds by oral intubation for 9 days and allowed to recover for 3 days. The animals were then meal fed from 8 a.m. to 4 p.m. for a period of 5 days, following which they were continued on the same meal schedule for an additional 6 days. During the 6-day period, the animals were administered the indicated compounds by oral intubation at 8 a.m. and 12 p.m. Body weight gain during the 6-day period was determined.

RESULTS

| Treatment | Geno-type[a] | Concentration mmoles/kg body weight b.i.d | Body Weight Gain g |
|---|---|---|---|
| Control | Fa/— | — | 9.5 ± 2.2[b] |
| Citric Acid | Fa/— | 1.32 | 2.8 ± 3.7 |
| (±)-threo-Chlorocitric acid | Fa/— | 1.32 | −22.9 ± 2.9* |
| (−)-threo-Chlorocitric acid | Fa/— | 0.66 | −20.7 ± 2.2* |
| (+)-threo-Chlorocitric acid | Fa/— | 0.66 | 2.5 ± 2.3* |
| Control | fa/fa | — | 5.8 ± 4.2 |
| Citric Acid | fa/fa | 1.32 | 3.4 ± 1.6 |
| (±)-threo-Chlorocitric acid | fa/fa | 1.32 | −27.9 ± 4.6* |
| (−)-threo-Chlorocitric acid | fa/fa | 0.66 | −33.5 ± 3.1* |
| (+)-threo-Chlorocitric acid | fa/fa | 0.66 | −3.6 ± 2.0 |

[a]Fa/—, lean rats; fa/fa, obese rats.
[b]Each value is the mean ± S.E.
*P ≤ 0.05

EXAMPLE 19

EFFECT OF (−)-threo-CHLOROCITRIC ACID ON BODY WEIGHT AND FOOD INTAKE IN MEAL-FED CHARLES RIVER RATS (16 DAY STUDY)

Two month old Charles River female rats (Charles River Breeding Laboratories, Wilmington, Mass.) were individually housed in wire-bottomed cages in a temperature-regulated (22° C.) light-controlled room (12 hr light, 6 a.m. to 6 p.m. and 12 hr dark, 6 p.m. to 6 a.m.). Three groups of rats (9 to 10 rats per group) were meal-fed a single meal daily of G-70 diet from 8 to 11 a.m. for 5 days; on the sixth day, they were treated as follows: (1) control, (2) (−)-threo-chlorocitric acid (1.0 mmoles/kg, 227 mg/kg) administered by oral intubation 30 min before the 3 hr meal, and (3) (−)-threo-chlorocitric acid (1.1 mmoles/kg, 250 mg/kg) as a dietary admixture for the 3 hr meal. Treatment was continued for 16 days. The amount of body weight gained and food consumed during the study were determined.

RESULTS

| Treatment | IBW[a] g | FBW[a] g | CBWG[a] g | CFC[a] g | Drug Ingested mmoles (mg)/kg/day |
|---|---|---|---|---|---|
| Control | 197 ± 2[b] | 219 ± 4 | 23 ± 2 | 211 ± 6 | — |
| (−)-threo-Chlorocitric acid (oral intubation) | 189 ± 3 | 163 ± 5*** | −27 ± 4*** | 139 ± 6*** | 1.0 (227) |

-continued

| Treatment | RESULTS | | | | Drug Ingested mmoles (mg)/kg/day |
|---|---|---|---|---|---|
| | IBW[a] g | FBW[a] g | CBWG[a] g | CFC[a] g | |
| (−)-threo-Chlorocitric acid (dietary admixture) | 192 ± 5 | 184 ± 8*** | −8 ± 6*** | 157 ± 9*** | 1.1 (250) |

[a]Abbreviations: IBW, initial body weight; FBW, final body weight; CBWG, cumulative body weight gain; CFC, cumulative food consumption.
[b]Each value is the mean ± S.E.
***$P \leq 0.001$

EXAMPLE 20

BODY COMPOSITION OF MEAL-FED CHARLES RIVER RATS ADMINISTERED (−)-threo-CHLOROCITRIC ACID (16 DAY STUDY)

Two month old Charles River female rats (Charles River Breeding Laboratories, Wilmington, Mass.) were individually housed in wire-bottomed cages in a temperature-regulated (22° C.) light-controlled room (12 hr light, 6 a.m. to 6 p.m. and 12 hr dark, 6 p.m. to 6 a.m.). Three groups of rats (9 to 10 rats per group) were meal-fed a single meal daily of G-70 diet from 8 to 11 a.m. for 5 days; on the sixth day, they were treated as follows: (1) control, (2) (−)-threo-chlorocitric acid (1.0 mmoles/kg, 227 mg/kg) administered by oral intubation 30 min before the 3 hr meal, and (3) (−)-threo-chlorocitric acid (1.1 mmoles/kg, 250 mg/kg as a dietary admixture for the 3 hr meal. Treatment was continued for 16 days.

After 16 days of treatment, rats were killed by decapitation and blood was removed. Carcasses were weighed, saponified in alcoholic potassium hydroxide, acidified, and extracted with petroleum ether according to the method described by A. C. Sullivan, et al, Am. J. Clinical Nutrition, 30 767 (1977). The petroleum ether supernatants were transferred to preweighed glass vials, evaporated immediately to dryness under nitrogen, and reweighed. Total carcass lipid data are expressed in grams and percentages of carcass weight. An aliquot of saponified carcass extract was neutralized and total carcass nitrogen was determined using the Kjeldahl procedure described in "Hawks" Physiological Chemistry," B. L. Oser, ed., McGraw Book Co., New York, N.Y., 1965, page 1214. Carcass protein data are expressed in grams and percentages of carcass weight.

| Treatment | Dose mmoles (mg)/kg | RESULTS | | | | |
|---|---|---|---|---|---|---|
| | | Carcass Weight[a] g | Carcass Lipid | | | Carcass Nitrogen |
| | | | total (g) | % of carcass weight | total (g) | % of carcass weight |
| Control | — | 207 ± 4[b] | 9.23 ± 0.79 | 4.44 ± 0.36 | 8.92 ± 0.32 | 4.31 ± 0.13 |
| (−)-threo-Chlorocitric acid (oral intubation) | 1.0 (227) | 155 ± 4*** | 2.74 ± 0.19*** | 1.94 ± 0.13*** | 6.57 ± 0.30 | 4.27 ± 0.22 |
| (−)-threo-Chlorocitric acid (dietary admixture) | 1.1 (250) | 176 ± 8** | 7.01 ± 0.92 | 4.01 ± 0.45 | 7.16 ± 0.29 | 4.10 ± 0.14 |

[a]Carcass includes body minus blood.
[b]Each value is the mean ± S.E.
**$P \leq 0.01$
***$P \leq 0.001$

EXAMPLE 21

EFFECT OF (−)-threo-CHLOROCITRIC ACID (ORAL ADMINISTRATION) ON BODY WEIGHT AND FOOD INTAKE IN MEAL-FED CHARLES RIVER RATS (17 DAY STUDY)

Two month old Charles River female rats (Charles River Breeding Laboratories, Wilmington, Mass.) were individually housed in wire-bottomed cages in a temperature-regulated (22° C.) light-controlled room (12 hr light, 6 a.m. to 6 p.m. and 12 hr dark, 6 p.m. to 6 a.m.). The animals (8 groups of 6 to 10 rats per group) were meal-fed a single meal daily of G-70 diet or chow from 8 a.m. to 11 a.m. for 7 days. On the 8th day, the animals were administered water or (−)-threo-chlorocitric acid at the indicated concentration by oral intubation 30 min before the 3 hr meal. Treatment was continued for 17 days. Food cups were weighed immediately after the meal. The amount of body weight gained and food consumed during the period was determined.

| Treatment | Diet | RESULTS | | | | |
|---|---|---|---|---|---|---|
| | | Dose mmoles (mg)/kg | IBW[a] g | FBW[a] g | CBWG[a] g | CFC[a] g |
| Control | G-70 | — | 199 ± 6[b] | 217 ± 5 | 18 ± 2 | 220 ± 7 |
| (−)-threo-Chlorocitric acid | | 0.25 (57) | 198 ± 4 | 211 ± 7 | 12 ± 4 | 209 ± 10 |
| | | 0.50 (114) | 195 ± 4 | 188 ± 7** | −6 ± 6** | 176 ± 9*** |
| | | 1.00 (227) | 198 ± 3 | 169 ± 6*** | −29 ± 6*** | 153 ± 4*** |
| Control | Chow | — | 199 ± 5 | 217 ± 6 | 19 ± 3 | 209 ± 5 |
| (−)-threo-Chlorocitric acid | | 0.25 (57) | 214 ± 7 | 213 ± 7 | −1 ± 4*** | 186 ± 9* |
| | | 0.50 (114) | 209 ± 5 | 177 ± 6*** | −32 ± 6*** | 165 ± 9*** |

-continued

| Treatment | Diet | Dose mmoles (mg)/kg | IBW[a] g | FBW[a] g | CBWG[a] g | CFC[a] g |
|---|---|---|---|---|---|---|
| | | 1.00 (227) | 207 ± 3 | 176 ± 11** | −30 ± 7*** | 130 ± 13*** |

[a]Abbreviations: IBW, initial body weight; FBW, final body weight; CBWG, cumulative body weight gain; CFC, cumulative food consumption.
[b]Each value is the mean ± S.E.
*$P \leq 0.05$
**$P \leq 0.01$
***$P \leq 0.001$

EXAMPLE 22

EFFECT OF (−)-threo-CHLOROCITRIC ACID (ORAL ADMINISTRATION) ON TOTAL BODY FAT IN MEAL-FED CHARLES RIVER RATS (17 DAY STUDY)

Two month old Charles River female rats (Charles River Breeding Laboratories, Wilmington, Mass.) were individually housed in wire-bottomed cages in a temperature-regulated (22° C.) light-controlled room (12 hr light, 6 a.m. to 6 p.m. and 12 hr dark, 6 p.m. to 6 a.m.). The animals (8 groups of 6 to 10 rats per group) were meal-fed a single meal daily of G-70 diet or chow from 8 a.m. to 11 a.m. for 7 days. On the 8th day, the animals were administered water or (−)-threo-chlorocitric acid at the indicated concentration by oral intubation 30 min before the 3 hr meal. Treatment was continued for 17 days. Food cups were weighed immediately after the meal.

After 17 days of treatment, rats were killed by decapitation and blood was removed. Carcasses and livers were weighed, saponified in alcoholic potassium hydroxide, acidified, and extracted with petroleum ether according to the method described by A. C. Sullivan, et al, Am. J. Clinical Nutrition, 30 767 (1977). The petroleum ether supernatants were transferred to preweighed glass vials, evaporated immediately to dryness under nitrogen, and reweighed. Total carcass and lipid data are expressed in grams and percentages of carcass weight.

EXAMPLE 23

EFFECT OF STEREOISOMERS OF CHLOROCITRIC ACIDS ON LIPID SYNTHESIS IN ISOLATED RAT HEPATOCYTES

Fatty Acid and Cholesterol Synthesis and $CO_2$ Production in Isolated Hepatocytes Female Charles River rats were fasted 48 hr, then meal-fed a 1% corn oil, 70% glucose diet for 7 to 14 days from 8 to 11 a.m. The isolated rat hepatocytes were prepared by perfusing the liver in situ. The hepatocytes were incubated in an oscillating water bath at 37° C. for 60 min. Each flask contained a total of 2.1 ml volume, consisting of 1 ml isolated rat hepatocytes (10–20 mg dry weight cells), 1 ml Krebs-Henseleit bicarbonate buffer pH 7.4, 16.5 mM glucose, 1$\mu$ mole L-alanine, 1$\mu$ Ci [U-$^{14}$C]alanine, 1 mCi $^3H_2O$, and 2 mM inhibitor in $H_2O$ at pH 7.4. All incubations were done in triplicate and all experiments were repeated at least twice. $CO_2$ was collected in each flask following the 60 min incubation by adding 0.3 ml ethanolamine:2-methoxyethanol (1:2) to the center well, 0.4 ml of 62.5% citric acid to the cell media, and incubating for 45 min. The contents of the center well were transferred to scintillation counting fluid and $^{14}CO_2$ content was determined. Ther media was saponified, extracted with hexane, precipitated with digitonin, washed, and counted (to determine the rate of cholesterogenesis). The media was then acidified, extracted with hexane, and the extract counted (to determine the rate of lipogenesis). The conversion of $^3H_2O$ and [$^{14}$C]alanine into fatty acids or sterols was determined in a PDS/3, Mark II liquid scintillation counting system. Data were expressed as nmoles $^3H_2O$ and [$^{14}$C]alanine converted into fatty acids or cholesterol, and nmoles [$^{14}$C]alanine oxidized to $^{14}CO_2$ per mg dry weight cells per 60 min.

RESULTS

| Treatment | Diet | Dose mmoles (mg)/kg | Carcass Weight[a] g | Carcass Lipid[a] total (g) | % of control | % carcass weight | % of control |
|---|---|---|---|---|---|---|---|
| Control | G-70 | — | — | 11.8 ± 1.97 | 100 | 5.43 ± 0.88 | 100 |
| (−)-threo-Chlorocitric acid | | 0.25 ( 57) | 196 ± 4** | 8.98 ± 0.30 | 76 | 4.58 ± 0.09 | 84 |
| | | 0.50 (114) | 177 ± 2*** | 7.85 ± 1.03 | 67 | 4.43 ± 0.56 | 82 |
| | | 1.00 (227) | 169 ± 6*** | 5.95 ± 1.28* | 50 | 3.48 ± 0.68 | 64 |
| Control | Chow | — | 208 ± 3 | 9.56 ± 1.23 | 104 | 4.62 ± 0.63 | 100 |
| (−)-threo-Chlorocitric acid | | 0.25 ( 57) | 213 ± 4 | 9.64 ± 0.80 | 101 | 4.56 ± 0.42 | 99 |
| | | 0.50 (114) | 173 ± 4*** | 4.80 ± 0.48** | 50 | 2.70 ± 0.17* | 58 |
| | | 1.00 (227) | 163 ± 7*** | 3.92 ± 0.37*** | 41 | 2.40 ± 0.22** | 52 |

[a]Carcass includes body minus 4 to 5 ml of blood.
[b]Each value is the mean ± S.E.
*$P \leq 0.05$
**$P \leq 0.01$
***$P \leq 0.001$

| | | RESULTS | | | | |
|---|---|---|---|---|---|---|
| | | Fatty Acid Synthesis | | Cholesterol Synthesis | | $CO_2$ Production |
| Compound | Dose mM | $^3H_2O$ converted % of control | [$^{14}$C]alanine converted % of control | $^3O$ converted % of control | [$^{14}$C]alanine converted % of control | [$^{14}$C]alanine converted % of control |
| Control | — | 100 | 100 | 100 | 100 | 100 |
| Trisodium (−)-threo-hydroxycitrate | 2 | 54** | 30** | 60** | 18*** | 103 |
| (+)-threo-Chlorocitric acid | 2 | 93 | 102 | 60*** | 69*** | 114*** |
| (−)-threo-Chlorocitric acid | 2 | 106 | 124* | 116 | 88* | 83* |
| (−)-threo-Chlorocitric acid | 2 | 95 | 96 | 98 | 92 | 91 |
| (+)-threo-Chlorocitric acid | 2 | 94 | 97 | 120 | 88** | 100 |

*$P \leq 0.05$
**$P \leq 0.01$
***$P \leq 0.001$

EXAMPLE 24

EFFECTS OF (±)-threo-CHLOROCITRIC ACID COMPARED TO TRISODIUM (−)-threo-HYDROXYCITRATE ON FATTY ACID SYNTHESIS IN PAIR-FEEDING EXPERIMENTS Female rats of the Charles River CD strain (Charles River Breeding Laboratories, Wilmington, Mass.) weighing 120–160 g (ca. 16 week old) were housed individually in wire-bottomed cages in a temperature-regulated (22° C.), light-controlled room (12 hour light 6 A.M.-6 P.M., and dark 6 P.M.-6 A.M.). They had free access to water and were fed a commercial diet (Purina Rodent Chow, Ralston Purina Co., St. Louis, Mo.) ad libitum for at least 1 week prior to the experiment. Animals were fasted 48 hours, then meal-fed a synthetic diet (G-70) daily from 8–11 A.M. for the remainder of the experiment. Food consumption and body weight were measured during the meal-feeding period. Body weights were randomized, so that each experimental group had an identical weight spread. Food spillage was measured daily.

Each group consisted of 8 to 10 (140 to 160 g) rats. Food intake was monitored for a 3 day period; the animals were dosed immediately before the 3 hr meal. Pair-fed animals were fed the amount of food which the drug treated groups ate on the previous days (days 2 and 3).

Immediately after the 3 hour feeding period, rats were administered intravenously a 0.25 ml saline (pH 7.4 to 7.6) solution with the following composition: 12.3 mg alanine, 5μCi [$^{14}$C] alanine (specific activity=156 mCi/mmole), 30.6 mg - ketoglutarate (as an amine acceptor for transaminase) and 1 mCi [$^3$H] water (specific activity=100 mCi/g). Experiments indicated that [$^{14}$C] lactate as a carbon precursor for lipogenesis. [$^3$H] Water was employed to determine the total rate of lipogenesis, since tritium is incorporated into fatty acids independent of the source of carbon precursors. Animals were killed by decapitation and blood collected in centrifuge tubes 30 minutes after the radioactive pulse, unless otherwise indicated. The specific radioactivity of the body water of each rat was determined by counting a diluted serum aliquot in 10 ml following cocktail: toluene (2.41), 2-methoxyethanol (1.61), naphthalene (320 g), and BBOT (2, 5-bis-2-(5-tert-butylbenzoxazolyl)-thiophene, 16 g). Liver, and small intestine was excised rapidly, weighed, and homogenized in 15 ml $H_2O$ in a Virtis 45 Macro Homogenizer for 15 sec at ca. 30,000 rpm. Duplicate 3 ml aliquots of whole homogenates were saponified, extracted, and the absolute radioactivity (dpm) determined. Liver lipids were extracted totally or separated into fatty acids and cholesterol by anion exchange chromatography. It was determined by anion exchange chromatography that the total lipid extract of liver contained fatty acids (96–97%) and cholesterol (3–4%). Data are expressed as nmoles [$^{14}$C] alanine or μ moles [$^3$H] water converted into lipid/g tissue/30 minutes. The nmoles [$^{14}$C] alanine were calculated according to the injected load of alanine, as reported previously by A. C. Sullivan et al., Arch. Biochem. and Biophys., 150, 183 (1972). The μ moles [$^3$H] water were determined as described previously by A. C. Sullivan et al., Lipids, 9, 121 (1974).

| | RESULTS | |
|---|---|---|
| | Fatty Acid Synthesis | |
| Treatment | Dose[a] mmoles/kg | μmoles $^3H_2O$ converted/ g liver/30 min | nmoles [$^{14}$C]alanine converted/ g liver/30 min |
| Pair-fed control | — | 21.3 ± 2.3[b] | 714 ± 86 |
| Trisodium (−)-threo-hydroxycitrate | 2.63 | 14.4 ± 1.6* | 279 ± 36** |
| Pair-fed control | — | 25.6 ± 3.9 | 639 ± 69 |
| (±)-threo-Chlorocitric acid | 1.32 | 21.4 ± 1.6 | 809 ± 67 |

[a]Doses were selected to produce a comparable reduction in food intake.
[b]Each value is the mean ± S.E.
*$P \leq 0.05$
**$P \leq 0.01$

EXAMPLE 25

EFFECT OF CHLOROCITRIC STEREOISOMERS ON STOMACH EMPTYING

Rats were trained to consume a 3 hr 70% glucose meal from 8 a.m. to 11 a.m. daily. On the experimental day, compounds were administered orally by intubation 30 min before a [$^{14}$C] glucose load was given also by intubation. The [$^{14}$C] glucose load consisted of 1.25 μCi [U-$^{14}$C] glucose and 1.0 g glucose dissolved in water. Sixty minutes later the rats were killed by decapitation; blood and stomachs were collected on ice. Serum was analyzed for [$^{14}$C] radioactivity as follows: 0.5 ml of serum was added to 10 ml of BBOT, an aqueous scintillation counting system (toluene [2.4 l], 2-methoxyethanol [1.6 l], naphthalene [320 g] and BBOT[2,5-bis-t-[5-tert-butylbenzoxazolylthiophine] [16 g], and radioactivity determined. Stomachs were cut longitudinally and washed exhaustively with saline. Total volume of stomach contents was measured and 0.5 ml was added to 10 ml of BBOT, and radioactivity was determined.

Data are expressed as follows: dpm×$10^3$ per ml of serum and dpm×$10^3$ per stomach.

RESULTS

| Treatment | Dose mmoles (mg)/kg | Stomach Contents dpm × $10^3$ total per stomach | % of control | Serum dpm × $10^3$ total per ml | % of control |
|---|---|---|---|---|---|
| Control | — | 884 ± 145[a] | 100 | 5.7 ± 0.3 | 100 |
| Trisodium Citrate | 0.33 (97) | 1180 ± 208 | 133 | 6.4 ± 0.1 | 112 |
| Trisodium (−)-hydroxycitrate | 0.33 (101) | 1973 ± 154*** | 223 | 4.5 ± 0.3* | 79 |
| (+)-threo-Chlorocitric acid | 0.33 (75) | 1946 ± 361* | 220 | 3.4 ± 0.6* | 60 |
| (−)-threo-Chlorocitric acid | 0.33 (75) | 2760 ± 69*** | 312 | 1.9 ± 0.4*** | 33 |
| (−)-erythro-Chlorocitric acid | 0.33 (75) | 1491 ± 232 | 169 | 5.1 ± 0.4 | 90 |
| (+)-erythro-Chlorocitric acid | 0.33 (75) | 1832 ± 1600** | 207 | 5.0 ± 0.4 | 88 |

[a]Each value is the mean ± S.E.
*P ≦ 0.05
**P ≦ 0.01
***P ≦ 0.001

EXAMPLE 26

EFFECT OF ORAL ADMINISTRATION OF (±)-threo-CHLOROCITRIC ACID (+)-threo-CHLOROCITRIC ACID AND (−)-threo-CHLOROCITRIC ACID ON FOOD INTAKE IN DOGS[a]

Twelve beagle dogs of both sexes weighing 7.6–12.2 kg were used for this test. The test compounds were contained in gelatin capsules for oral administration to two dogs of each sex. The animals were weighed and food consumption calculated daily excluding weekends throughout the test period. Each animal received 800 grams of diet daily consisting of 400 grams of Wayne pellet dog food mixed with 400 ml distilled water. The animals received pyramiding oral doses of the test compound over the three week period. On Monday and Tuesday of the first week the animals were weighed and food consumption was recorded (control). The animals received 3 mg/kg on Wednesday and 10 mg/kg on Friday of the first week. Doses of 30, 100 and 300 mg/kg were administered on Monday, Wednesday and Friday respectively during the second week. A final dose of 1000 mg/kg was administered on Monday of the third week.

RESULTS

| Test Day | Dose | (±)-threo-Chlorocitric acid g | (+)-threo-Chlorocitric acid g | (−)-threo-Chlorocitric acid g |
|---|---|---|---|---|
| −2, −1 | — | 479 ± 96[c] | 610 ± 43 | 743 ± 54 |
| 1 | 3 | 616 ± 79 | 430 ± 109 | 450 ± 165* |
| 2 | — | 392 ± 140 | 502 ± 109 | 646 ± 83 |
| 3 | 10 | 460 ± 136 | 367 ± 114* | 440 ± 121* |
| 6 | 30 | 511 ± 104 | 629 ± 64 | 406 ± 86** |
| 7 | — | 479 ± 116 | 397 ± 87* | 668 ± 115 |
| 8 | 100 | 299 ± 176 | 477 ± 75 | 142 ± 38*** |
| 9 | — | 492 ± 110 | 585 ± 69 | 619 ± 62 |
| 10 | 300 | 316 ± 109 | 436 ± 60 | 55 ± 39*** |
| 13 | 1000 | 164 ± 61* | 433 ± 125 | 56 ± 22*** |
| 14 | — | 560 ± 136 | 518 ± 19 | 439 ± 163* |
| 15 | — | 543 ± 92 | 622 ± 69 | 583 ± 149 |
| 16 | — | 624 ± 88 | 564 ± 106 | 600 ± 76 |
| 17 | — | 645 ± 93 | 597 ± 36 | 677 ± 73 |
| 20 | — | 800[a] | 583 ± 17[b] | 607 ± 193[b] |
| 21 | — | 561 ± 83 | 578 ± 79 | 644 ± 100 |
| 22 | — | 649 ± 91 | 668 ± 57 | 800 ± 0 |
| 23 | — | 533 ± 118 | 516 ± 66 | 596 ± 121 |
| 24 | — | 477 ± 114 | 539 ± 39 | 695 ± 79 |
| 27 | — | 518 ± 139 | 479 ± 92 | 732 ± 68 |
| 28 | — | 663 ± 137 | 710 ± 91 | 775 ± 26 |

[a]One animal.
[b]Two animals.
[c]Each value is the mean ± S.E.
*P ≦ 0.05
**P ≦ 0.01
***P ≦ 0.001

EXAMPLE 27

EFFECT OF ORAL ADMINISTRATION OF (±)-threo-CHLOROCITRIC ACID, (±)-threo-CHLOROCITRIC ACID, AND (−)-threo-CHLOROCITRIC ACID ON FOOD INTAKE IN DOGS Food intake was determined by the procedure at pyramiding doses described in EXAMPLE 26.

RESULTS

| Test Day | Dose | (±)-threo-Chlorocitric acid % of control | (+)-threo-Chlorocitric acid % of control | (−)-threo-Chlorocitric acid % of control |
|---|---|---|---|---|
| −2, −1 | — | 100 | 100 | 100 |
| 1 | 3 | 129 | 70 | 60* |
| 2 | — | 82 | 82 | 87 |
| 3 | 10 | 96 | 60* | 59* |
| 6 | 30 | 107 | 103 | 55*** |
| 7 | — | 100 | 65* | 90 |
| 8 | 100 | 62 | 78 | 19*** |
| 9 | — | 103 | 96 | 83 |
| 10 | 300 | 66 | 71 | 7*** |
| 13 | 1000 | 34* | 71 | 8*** |
| 14 | — | 117 | 85 | 59* |
| 15 | — | 113 | 102 | 78 |
| 16 | — | 130 | 92 | 81 |
| 17 | — | 135 | 98 | 91 |
| 20 | — | 167[a] | 96[b] | 82[b] |
| 21 | — | 117 | 95 | 87 |
| 22 | — | 135 | 110 | 108 |
| 23 | — | 111 | 85 | 80 |
| 24 | — | 100 | 88 | 94 |
| 27 | — | 108 | 79 | 99 |
| 28 | — | 138 | 116 | 104 |

[a]One animal.
[b]Two animals.
*P ≦ 0.05
**P ≦ 0.01
***P ≦ 0.001

EXAMPLE 28

| COMPOSITION | |
|---|---|
| | Amount (mg/tablet) |
| The composition was prepared as follows: | |
| (−)-threo-Chlorocitric acid | 50 |
| Polyvinylpyrrolidone | 2 |
| Microcrystalline Cellulose (Avicel PH 101) | 10 |
| Silicone Dioxide (Safoid 244) | 1 |
| Magnesium Stearate | 1 |

(−)-threo-Chlorocitric acid was passed through a Fitzpatrick Comminuting Machine using a No. 1B plate, knives forward at medium speed. The milled compound was granulated with a 40% (weight/weight) solution of polyvinylpyrrolidone in 2-propanol. The granulation was then passed through the Fitzpatrick machine using a No. 4 plate, knives foward at slow speed, and dried overnight at 55° C. to a granulation moisture content of equal to or less then 0.5%. The dried granulation was milled as before using No. 2A plates, knives forward at slow speed. Microcrystalline cellulose and silicone droxide was added to the dry granulation and mixed for ten minutes. Magnesium stearate was then added and mixing was continued for an additional 5 minutes. Upon completion of the mixing, the formulation was compressed on a conventional tabletting machine.

EXAMPLE 29

Mono-potassium (±)-threo-epoxyaconitate monohydrate (a) Chlorination-Method.

A stock solution of potassium hydroxide and water was prepared by adding 1320 g of potassium hydroxide pellets (ca. 85%) to 1000 ml of water followed by the addition of 1500 g of ice. The solution was found to contain 5.25 meq of potassium hydroxide per gram of solution and was stored in a Nalgene container.

To 550 g (2.9 mol) of the stock solution was added 174 g (1.0 mol) of trans aconitic acid portionwise over ca. 20 min, with cooling by the addition of ice pellets (100 g). The pH of the resulting solution was adjusted to a value of 7.2 by the dropwise addition of ca. 21 g (ca. 0.1 mol) of the stock potassium hydroxide solution. Chlorine gas was added to the reaction mixture cooled to about 5° to 7° by means of an external acetone-dry ice bath, with stirring. After about 15 min, chlorine gas was no longer absorbed by the reaction mixture. The flow of chlorine gas was stopped, the reaction mixture was stirred for 10 to 15 min at about 7° and the excess chlorine gas was purged using argon. The reaction mixture was cooled to about 20° and 135 g (about 2.05 mol) of potassium hydroxide pellets (85%) were added in one portion with stirring. After stirring for about 5 min the resulting solution was cooled to 25° and the pH of the reaction mixture was adjusted to a value of about 7.2 by the dropwise addition of concentrated hydrochloric acid. 12 N Hydrochloric acid (166 ml, 2.0 mol) was then added and the solution was stored in a refrigerator at 0° to 5° overnight. The resulting precipitate was collected on a filter and washed with cold ethanol-water (1:1) and ethanol. The filter cake was dried at 40° under house vacuum to give 245 g of a mixture of the mono-potassium salt of (±)-threo-epoxyaconitic acid as the monohydrate and potassium chloride. The solid material was dissolved in 400 ml of water at 60° and 300 ml of ethanol was added. The mixture was cooled to about 5° and the solids were collected and washed with cold ethanol-water (1:1) and ethanol to yield 169 g of mono-potassium (±)-threo-epoxyaconitate monohydrate, having a neutralization equivalent of 123.6 g/equiv.

The product may be purified by recrystallization from water.

(b) Hypochlorination Method.

Chlorine gas was added to 419 g (2.2 mol) of the stock potassium hydroxide solution and 75 ml of water cooled to 0°. The reaction mixture was filtered to remove precipitated potassium chloride and the filtrate was added dropwise over about 15 min to a stirred solution of 174 g (1.0 mol) of trans aconitic acid, 362 g (1.9 mol) of the stock potassium hydroxide solution and 250 g of ice maintained at a reaction temperature between −5° to 0°. The reaction mixture was stirred at 0° for about 15 min and 7.0 g (0.1 mol) of chlorine gas was added by means of a gas dispersion tube as rapidly as possible. The reaction mixture was purged of residual chlorine gas by means of argon, cooled to about 0° and 75 g (ca. 1.1 mol) of potassium hydroxide pellets (85%) were added in one portion with stirring. The mixture was heated at 50° for about 10 min, cooled to about 25° and the pH of the solution was adjusted to a value of about 7.2 by the dropwise addition of hydrochloric acid. Upon completion of the pH adjustment, 166 ml (2.0 mol) of 12 N hydrochloric acid was added with stirring and the solution was stored at 0° for 16 hours. The precipitate was collected and washed with cold ethanol-water (1:1) and ethanol. The filter cake was dissolved in 350 ml of water and the stirred solution was heated to 60°. Ethanol (ca. 300 ml) was added and the mixture was stirred at 0° for 2 hours. The precipitate was collected and washed with cold ethanol-water (1:1) and ethanol to give, after drying to constant weight, 158 g of the mono-potassium salt of (±)-threo-epoxyaconitic acid as the monohydrate having a neutralization equivalent of 123.4 g/equiv.

(c) Alternative Hypochlorination Method.

To a solution of 116 g (0.67 mol) of trans aconitic acid, 370 g (ca. 1.94 mol) of the stock potassium hydroxide solution (as prepared in method (b) and 250 g of ice, 11.4 g (ca. 0.06 mol) of the stock potassium hydroxide solution was added dropwise to adjust the pH to the value of 7.2. To the resulting solution was added the stock potassium hypochloride in one portion at about −10°. trans Aconitic acid (58.1 g, 0.33 mol) was added in ca. 3 g portions to the stirred solution over ca. 15 min so that the reaction temperature did not exceed −5°. After the addition was complete, 8.3 ml (0.1 mol) of conc hydrochloric acid was added dropwise to the stirred solution. The reaction mixture was stirred at 0° for an additional 13 min and 7.0 g (ca. 0.1 mol) of chlorine gas was added rapidly by means of a gas dispersion tube. After 5 min the reaction mixture was purged by argon gas and 75 g (ca. 1.1 mol) of potassium hydroxide pellets (85%) were added in one portion. The reaction mixture was stirred at 50° for 15 min, cooled to room temperature and the pH was adjusted to a value of about 7.2 by the dropwise addition of concentrated hydrochloric acid. 12 N Hydrochloric acid (166 ml, 2.0 mol) was then added with stirring and the resulting solution was stored at 5° overnight. The precipitate was collected and washed with cold ethanol-water (1:1) and ethanol. The filter cake was dissolved in 350 ml of water and diluted with 300 ml of ethanol. The solution was cooled to about 5° and after 2 hours the precipitate was collected and washed with cold ethanol-water (1:1) and ethanol to give, after drying to constant weight, 161 g of mono-potassium salt of (±)-threo-epoxyaconitic acid having a neutralization equivalent of 123.6 g/equiv.

(d) Peroxidation Method.

Sodium tungstate monohydrate (33.0 g, 0.1 mol) in ca. 75 ml of deionized water was passed through a prewashed column of 150 ml (0.3 equiv) of Amberlite IR 120 A ion-exchange resin (hydrogen ion form, ca. 2 equiv/ml) and the column was washed with 125 ml of deionized water. The combined eluates were added to a solution of 348 g (2.0 mol) of trans aconitic acid and 800 ml of deionized water maintained at a temperature of 62°. Upon completion of the addition of the combined eluates, 250 ml (2.5 mol) of 30% of hydrogen peroxide solution was added in one portion. The reaction mixture was stirred for 30 min and an additional 75 ml of 30% of hydrogen peroxide solution was added in one portion at a reaction temperature of about 65°. After 4 hours, the solution was cooled to 50° and 400 g (2.1 mol) of the stock potassium hydroxide solution was added with stirring. Ethanol (1.3 l) was added and the mixture was cooled to 0° with stirring. After 3 hours the precipitate was collected and washed with cold ethanol-water (1:1) and ethanol to give, after drying to constant weight, 406 g of mono-potassium(±)-threo-epoxyaconitic acid monohydrate.

EXAMPLE 30

(±)-threo-Epoxyaconitic acid.

Concentrated sulfuric acid (102.2 g, 1.0 mol) was added dropwise to a solution of 246 g (1.0 mol) of mono-potassium (±)-threo-epoxyaconitic acid, monohydrate, and 450 ml of acetone, with stirring at 20° to 23°. After the addition was complete, the reaction mixture was stirred at room temperature for an additional 30 min. The precipitated potassium hydrogen sulfate was collected and washed with acetone. The combined filtrate and washings were heated under reflux and 1.0 l of warm (ca. 60°) 1,2-dichloroethane was added with stirring. The stirred solution was boiled and the volume was maintained at about 1.5 l by the periodic addition of 1,2-dichloroethane, until the product began to crystallize from solution. The mixture was cooled to about 5° and, after stirring for about 2 hours, the precipitate was collected and washed with acetone-1,2-dichloroethane (1:4) to give 151 g of (±)-threo-epoxyaconitic acid as the sesquihydrate.

The combined mother liquors were concentrated to a final volume of about 1 l and the precipitate was collected and washed with acetone-1,2-dichloroethane (1:4) to give 45.8 g of the product as the monohydrate.

Concentration of the mother liquors and treatment of the precipitate as hereinbefore described afforded an additional 10.4 g of the monohydrate.

EXAMPLE 31

Resolution of (±)-threo-epoxyaconitic acid.

A solution of 38.0 g (0.2 mol) of (±)-threo-epoxyaconitic acid, 59.8 g (0.36 mol) of (+)-p-nitro-α-methylbenzylamine and 350 ml of water-methanol (1:49) was stirred at room temperature for 2 hours and stored at 0°–5° for 16 hours. The precipitate was collected, washed with water-methanol (1:49) to afford, after drying water vacuum, 55.5 g of crude product. Recrystallization of the salt from water-methanol (1:49) gave 44.8 g of (+)-threo-epoxyaconitic acid, bis (+)-p-nitro-α-methylbenzylamine salt, having $[\alpha]_{436\ mm}^{25°\ C.}+15.02°$ (c, 2.0, water).

To a solution of 160 ml (0.181 mol) of 1.13 M hydrogen chloride and ether, under an inert atmosphere, 44.4 g (0.082 mol) of the above-obtained product was added portionwise with stirring at ca. 12°. The reaction mixture was allowed to warm to room temperature and was stirred at room temperature for 30 min. The precipitate was collected, washed with ether and air dried to give 33 g of (+)-threo-epoxyaconitic acid.

The filtrates were combined and concentrated to dryness under reduced pressure. The residue was dissolved in hot ethyl acetate (about 70°) and about 60 ml of carbon tetrachloride was added with stirring to the cloud point. The mixture was allowed to cool to room temperature and was stored in a refrigerator overnight. The precipitate was collected, washed with ethyl acetate-carbon tetrachloride (1:3) and air dried to give an additional 16.4 g of product.

The (+)-threo-epoxyaconitic acid, monohydrate, so obtained had m.p. 108°–110°, $[\alpha]_{25}^D +11.5°$ (c, 1.0 methanol) and neut equiv of 69.32 g/equiv.

We claim:

1. A process for the preparation of a chlorocitric acid of the formula

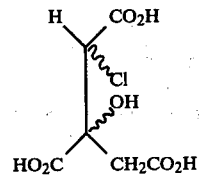

and stereoisomers and optical antipodes thereof which comprises the step of contacting an epoxyaconitic acid of the formula

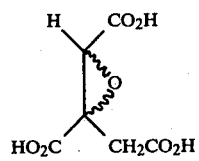

and stereoisomers and optical antipodes thereof, with an alkali metal chloride or an alkaline earth metal chloride in an aqueous solvent in the presence of about one molar equivalent of hydrochloric acid at a reaction temperature of about 50° C. to 80° C.

2. The process of claim 1 wherein (±)-threo-epoxyaconitic acid of the formula

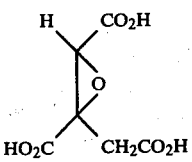

affords (±)-threo-chlorocitric acid of the formula

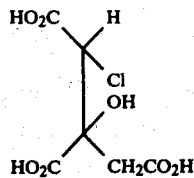

3. The process of claim 1 wherein (±)-erythro-epoxyaconitic acid of the formula

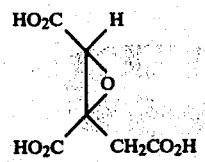

affords (±)-erythro-chlorocitric acid of the formula

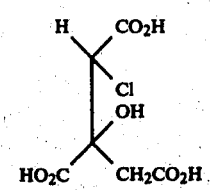

4. The process of claim 1 wherein (±)-threo-epoxyaconitic acid of the formula

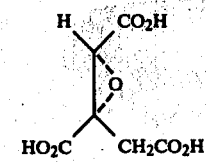

affords (−)-threo-chlorocitric acid of the formula

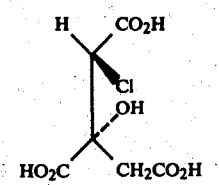

5. The process of claim 1 wherein (−)-threo-epoxyaconitic acid of the formula

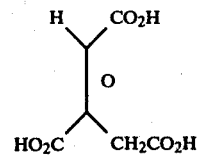

affords (+)-threo-chlorocitric acid of the formula

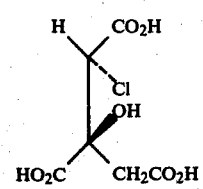

6. The process of claim 1 wherein (−)-erythro-epoxyaconitic acid of the formula

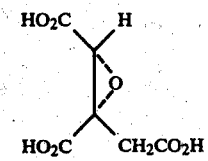

affords (+)-erythro-chlorocitric acid of the formula

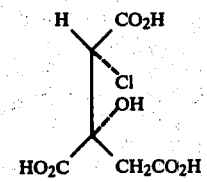

7. The process of claim 1 wherein (+)-erythro-epoxyaconitic acid of the formula

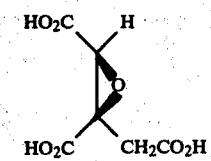

affords (−)-erythro-chlorocitric acid of the formula

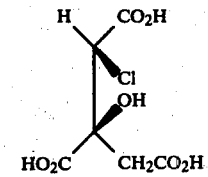

8. The process of claim 1 wherein an alkali metal chloride is employed.

9. The process of claim 1 wherein the alkali metal chloride is sodium chloride.

10. The process of claim 1 wherein the reaction temperature is about 70° C.

* * * * *